United States Patent
Johnson et al.

(10) Patent No.: US 10,699,247 B2
(45) Date of Patent: Jun. 30, 2020

(54) SYSTEMS AND METHODS FOR PROVIDING HEALTH TASK NOTIFICATIONS

(71) Applicant: Under Armour, Inc., Baltimore, MD (US)

(72) Inventors: Gwen Johnson, Austin, TX (US); Poojit Sharma, Austin, TX (US); Karthik Subramaniam, Austin, TX (US); Martin Price, Austin, TX (US); Scott Laing, Austin, TX (US)

(73) Assignee: Under Armour, Inc., Baltimore, MD (US)

( * ) Notice: Subject to any disclaimer, the term of this patent is extended or adjusted under 35 U.S.C. 154(b) by 507 days.

(21) Appl. No.: 15/596,572

(22) Filed: May 16, 2017

(65) Prior Publication Data

US 2018/0336530 A1    Nov. 22, 2018

(51) Int. Cl.
*G06Q 10/10*      (2012.01)
*G06Q 50/22*      (2018.01)

(52) U.S. Cl.
CPC ......... *G06Q 10/1093* (2013.01); *G06Q 50/22* (2013.01)

(58) Field of Classification Search
CPC ....... A61B 5/746; A61B 5/742; A61B 5/4818; A61B 5/4806; A61B 5/4812; A61B 5/4815; A61B 5/0022; G16H 40/63; G16H 50/20; G16H 10/60; G16H 40/67; G16H 20/60; G06Q 10/10; G06Q 10/1093; G06Q 10/107; G06Q 10/1097; G06Q 10/0639; G06Q 10/0631
See application file for complete search history.

(56) References Cited

U.S. PATENT DOCUMENTS

| | | |
|---|---|---|
| 6,306,088 B1 | 10/2001 | Krausman et al. |
| 6,878,121 B2 | 4/2005 | Krausman et al. |
| 8,083,643 B2 | 12/2011 | Ng et al. |
| 8,257,228 B2 | 9/2012 | Quatrochi |
| 8,446,275 B2 | 5/2013 | Utter |
| 8,468,115 B2 | 6/2013 | Gartenberg |
| 8,548,770 B2 | 10/2013 | Yuen et al. |
| 8,568,278 B2 | 10/2013 | Riley |
| 8,617,068 B2 | 12/2013 | Doherty et al. |
| 8,672,853 B2 | 3/2014 | Young |
| 8,702,430 B2 | 4/2014 | Dibenedetto et al. |
| 8,823,518 B2 | 9/2014 | Swope |
| 8,849,610 B2 | 9/2014 | Molettiere et al. |

(Continued)

*Primary Examiner* — Maroun P Kanaan
(74) *Attorney, Agent, or Firm* — Maginot, Moore & Beck LLP

(57) ABSTRACT

A method and system for providing health task notifications to users. In one embodiment, the method comprises establishing a schedule for the delivery of health task notifications or reminders. The schedule may be entered by the user or provided as an editable default schedule based on the user's inputted health goals. Notifications and/or reminders are then provided according to the schedule. The system includes a means by which the user may interact with the messages to provide a response. For example, the user may acknowledge, dismiss, and/or delay the message. Based on the user's interaction, the message display is completed or reiterated at a predetermined delay time. In some instances, the schedule may also be updated based on the user's response.

19 Claims, 9 Drawing Sheets

(56) References Cited

U.S. PATENT DOCUMENTS

| | | | |
|---|---|---|---|
| 8,852,098 B2 | 10/2014 | Teller et al. | |
| 8,858,400 B2 | 10/2014 | Johnson | |
| 8,868,377 B2 | 10/2014 | Yuen et al. | |
| 8,870,766 B2 | 10/2014 | Stivoric et al. | |
| 8,903,671 B2 | 12/2014 | Park et al. | |
| 8,920,332 B2 | 12/2014 | Hong et al. | |
| 8,935,119 B2 | 1/2015 | Yuen | |
| 8,945,017 B2 | 2/2015 | Venkatraman et al. | |
| 8,947,239 B1 | 2/2015 | Park | |
| 8,948,832 B2 | 2/2015 | Hong et al. | |
| 8,954,135 B2 | 2/2015 | Yuen et al. | |
| 8,956,303 B2 | 2/2015 | Hong et al. | |
| 8,961,413 B2 | 2/2015 | Teller et al. | |
| 8,961,414 B2 | 2/2015 | Teller et al. | |
| 8,968,196 B2 | 3/2015 | Teller et al. | |
| 8,971,936 B2 | 3/2015 | Derchak | |
| 8,979,763 B2 | 3/2015 | Stivoric et al. | |
| 8,998,815 B2 | 4/2015 | Venkatraman et al. | |
| 9,005,129 B2 | 4/2015 | Venkatraman et al. | |
| 9,011,153 B2 | 4/2015 | Bennett et al. | |
| 9,014,790 B2 | 4/2015 | Richards et al. | |
| 9,033,875 B2 | 5/2015 | Teller et al. | |
| 9,033,876 B2 | 5/2015 | Teller et al. | |
| 9,044,149 B2 | 6/2015 | Richards et al. | |
| 9,044,171 B2 | 6/2015 | Venkatraman et al. | |
| 9,050,488 B2 | 6/2015 | Brumback et al. | |
| 9,079,060 B2 | 7/2015 | Hong et al. | |
| 9,084,536 B2 | 7/2015 | Yuen et al. | |
| 9,087,234 B2 | 7/2015 | Hoffman | |
| 9,098,991 B2 | 8/2015 | Park et al. | |
| 9,113,794 B2 | 8/2015 | Hong et al. | |
| 9,113,795 B2 | 8/2015 | Hong et al. | |
| 9,113,823 B2 | 8/2015 | Yuen et al. | |
| 9,135,347 B2 | 9/2015 | Damman | |
| 9,143,203 B2 | 9/2015 | Park | |
| 9,165,117 B2 | 10/2015 | Teller et al. | |
| 9,168,001 B2 | 10/2015 | Stivoric et al. | |
| 9,168,419 B2 | 10/2015 | Hong et al. | |
| 9,173,576 B2 | 11/2015 | Yuen et al. | |
| 9,173,577 B2 | 11/2015 | Yuen et al. | |
| 9,198,604 B2 | 12/2015 | Venkatraman et al. | |
| 9,237,855 B2 | 1/2016 | Hong et al. | |
| 9,241,635 B2 | 1/2016 | Yuen et al. | |
| 9,242,142 B2 | 1/2016 | Vincent | |
| 9,248,340 B2 | 2/2016 | Hoffman | |
| 9,282,902 B2 | 3/2016 | Richards et al. | |
| 9,286,789 B2 | 3/2016 | Park et al. | |
| 9,307,351 B2 | 4/2016 | Park | |
| 9,307,917 B2 | 4/2016 | Hong et al. | |
| 9,317,660 B2 | 4/2016 | Burich et al. | |
| 9,410,979 B2 | 8/2016 | Yuen et al. | |
| 9,456,787 B2 | 10/2016 | Venkatraman et al. | |
| 2006/0026212 A1* | 2/2006 | Tsukerman | G06F 16/21 |
| 2008/0167536 A1 | 7/2008 | Teller et al. | |
| 2011/0054290 A1 | 3/2011 | Derchak | |
| 2012/0041767 A1 | 2/2012 | Hoffman | |
| 2012/0094258 A1 | 4/2012 | Langheier et al. | |
| 2013/0046151 A1 | 2/2013 | Bsoul et al. | |
| 2013/0072765 A1 | 3/2013 | Kahn et al. | |
| 2013/0130213 A1 | 5/2013 | Burbank | |
| 2013/0158367 A1 | 6/2013 | Pacione et al. | |
| 2013/0158368 A1 | 6/2013 | Pacione et al. | |
| 2013/0338446 A1 | 12/2013 | Van Vugt et al. | |
| 2013/0344465 A1 | 12/2013 | Dickinson et al. | |
| 2014/0058703 A1 | 2/2014 | Kimishima et al. | |
| 2014/0073486 A1 | 3/2014 | Ahmed et al. | |
| 2014/0076318 A1 | 3/2014 | Flower et al. | |
| 2014/0081666 A1 | 3/2014 | Teller et al. | |
| 2014/0107932 A1 | 4/2014 | Luna | |
| 2014/0122536 A1 | 5/2014 | Stivoric et al. | |
| 2014/0125491 A1 | 5/2014 | Park et al. | |
| 2014/0127996 A1 | 5/2014 | Park et al. | |
| 2014/0173082 A1 | 6/2014 | Shin | |
| 2014/0180137 A1 | 6/2014 | Stivoric et al. | |
| 2014/0206954 A1 | 7/2014 | Yuen et al. | |
| 2014/0213855 A1 | 7/2014 | Teller et al. |
| 2014/0213856 A1 | 7/2014 | Teller et al. |
| 2014/0221769 A1 | 8/2014 | Teller et al. |
| 2014/0221784 A1 | 8/2014 | Pacione et al. |
| 2014/0221788 A1 | 8/2014 | Teller et al. |
| 2014/0221789 A1 | 8/2014 | Pacione et al. |
| 2014/0221790 A1 | 8/2014 | Pacione et al. |
| 2014/0221791 A1 | 8/2014 | Pacione et al. |
| 2014/0223406 A1 | 8/2014 | Teller et al. |
| 2014/0266939 A1 | 9/2014 | Baringer et al. |
| 2014/0273858 A1 | 9/2014 | Panther et al. |
| 2014/0275812 A1 | 9/2014 | Stivoric et al. |
| 2014/0275813 A1 | 9/2014 | Stivoric et al. |
| 2014/0276192 A1 | 9/2014 | Stivoric et al. |
| 2014/0278139 A1 | 9/2014 | Hong et al. |
| 2014/0278220 A1 | 9/2014 | Yuen |
| 2014/0296656 A1 | 10/2014 | Kasama |
| 2014/0303523 A1 | 10/2014 | Hong et al. |
| 2014/0316305 A1 | 10/2014 | Venkatraman et al. |
| 2014/0323880 A1 | 10/2014 | Ahmed et al. |
| 2014/0330132 A1 | 11/2014 | Raskin |
| 2014/0342328 A1 | 11/2014 | Pacione et al. |
| 2014/0347366 A1 | 11/2014 | Emori et al. |
| 2014/0350356 A1 | 11/2014 | Ahmed et al. |
| 2014/0377729 A1 | 12/2014 | Yuen et al. |
| 2014/0378786 A1 | 12/2014 | Hong et al. |
| 2014/0378872 A1 | 12/2014 | Hong et al. |
| 2015/0038865 A1 | 2/2015 | Shigeto et al. |
| 2015/0066174 A1 | 3/2015 | Dugan |
| 2015/0066526 A1 | 3/2015 | Cheng et al. |
| 2015/0112158 A1 | 4/2015 | He et al. |
| 2015/0118669 A1 | 4/2015 | Wisbey et al. |
| 2015/0120019 A1 | 4/2015 | Wisbey et al. |
| 2015/0120025 A1 | 4/2015 | Wisbey et al. |
| 2015/0120203 A1 | 4/2015 | Wisbey et al. |
| 2015/0122018 A1 | 5/2015 | Yuen |
| 2015/0134268 A1 | 5/2015 | Yuen et al. |
| 2015/0173631 A1 | 6/2015 | Richards et al. |
| 2015/0173671 A1 | 6/2015 | Paalasmaa et al. |
| 2015/0182164 A1 | 7/2015 | Utter, II |
| 2015/0186609 A1 | 7/2015 | Utter, II |
| 2015/0196256 A1 | 7/2015 | Venkatraman et al. |
| 2015/0201854 A1 | 7/2015 | Hong et al. |
| 2015/0220697 A1 | 8/2015 | Hunt et al. |
| 2015/0220883 A1 | 8/2015 | B'Far et al. |
| 2015/0231446 A1 | 8/2015 | Brumback et al. |
| 2015/0238097 A1 | 8/2015 | Teller et al. |
| 2015/0245797 A1 | 9/2015 | Teller et al. |
| 2015/0245801 A1 | 9/2015 | Brumback et al. |
| 2015/0258375 A1 | 9/2015 | Riley |
| 2015/0258376 A1 | 9/2015 | Riley |
| 2015/0258377 A1 | 9/2015 | Riley |
| 2015/0258379 A1 | 9/2015 | Riley |
| 2015/0282767 A1 | 10/2015 | Stivoric et al. |
| 2015/0289797 A1 | 10/2015 | Pacione et al. |
| 2015/0289799 A1 | 10/2015 | Pacione et al. |
| 2015/0289800 A1 | 10/2015 | Pacione et al. |
| 2015/0289802 A1 | 10/2015 | Thomas et al. |
| 2015/0289803 A1 | 10/2015 | Wu et al. |
| 2015/0289808 A1 | 10/2015 | Pacione et al. |
| 2015/0289809 A1 | 10/2015 | Pacione et al. |
| 2015/0289810 A1 | 10/2015 | Pacione et al. |
| 2015/0289811 A1 | 10/2015 | Pacione et al. |
| 2015/0289812 A1 | 10/2015 | Pacione et al. |
| 2015/0294554 A1 | 10/2015 | Park et al. |
| 2015/0294574 A1 | 10/2015 | Pacione et al. |
| 2015/0294575 A1 | 10/2015 | Pacione et al. |
| 2015/0294576 A1 | 10/2015 | Pacione et al. |
| 2015/0294583 A1 | 10/2015 | Pacione et al. |
| 2015/0294594 A1 | 10/2015 | Pacione et al. |
| 2015/0314166 A1 | 11/2015 | Hong et al. |
| 2015/0339792 A1 | 11/2015 | Emori et al. |
| 2015/0339946 A1 | 11/2015 | Pacione et al. |
| 2016/0001159 A1 | 1/2016 | Riley |
| 2016/0015314 A1 | 1/2016 | Dusanter et al. |
| 2016/0015315 A1 | 1/2016 | Auphan et al. |
| 2016/0016041 A1 | 1/2016 | Giedwoyn |
| 2016/0034634 A9 | 2/2016 | Hong et al. |
| 2016/0036118 A1 | 2/2016 | Baringer et al. |

(56) References Cited

U.S. PATENT DOCUMENTS

| | | |
|---|---|---|
| 2016/0042142 A1 | 2/2016 | Arnold et al. |
| 2016/0045135 A1 | 2/2016 | Kim et al. |
| 2016/0051169 A1 | 2/2016 | Hong et al. |
| 2016/0058970 A1 | 3/2016 | Garcia Molina et al. |
| 2016/0066844 A1 | 3/2016 | Venkatraman et al. |
| 2016/0071423 A1 | 3/2016 | Sales et al. |
| 2016/0074707 A1 | 3/2016 | Thorpe et al. |
| 2016/0081616 A1 | 3/2016 | Li |
| 2016/0125160 A1 | 5/2016 | Heneghan et al. |
| 2016/0150978 A1 | 6/2016 | Yuen et al. |
| 2016/0151603 A1 | 6/2016 | Shouldice et al. |
| 2017/0352287 A1* | 12/2017 | Arnold .................. G09B 19/00 |

* cited by examiner

SYSTEMS AND METHODS FOR PROVIDING HEALTH TASK NOTIFICATIONS

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The device and method disclosed in this document relates health tracking devices and, more particularly, to health tracking devices configured to provide health task notifications.

BACKGROUND

Health tracking devices are increasingly utilized by individuals interested in tracking metrics related to their personal health and fitness activity. These health tracking devices include, for example, heart rate monitors, step counters, stair counters, global positioning system ("GPS") tracking devices, as well as various other motion and biometric tracking devices. Some health tracking devices include features designed to encourage and guide the user in achieving his or her health and fitness goals. Such features can sometimes improve the user's long-term adherence to his or her health and fitness plan and ultimately improve outcomes. However, such features can also become annoying to the user, resulting in the user disabling the features or abandoning use of the health tracking device entirely.

In view of the foregoing, it would be advantageous to provide a health tracking device having features that encourage and guide the user in achieving his or her health and fitness goals but are also flexibly implemented so as to not burden or annoy the user.

SUMMARY

In accordance with one exemplary embodiment of the disclosures, a method of operating a user device is disclosed. The method comprises: (i) storing a schedule for a display of a plurality of health task reminders to a user; (ii) displaying one of the plurality of health task reminders on a display device of the user device at a first day and/or time based on the schedule; (iii) receiving user input relating to the health task reminder via an input device of the user device; (iv) performing an action based on the user input; (v) determining, based at least in part on the data indicative of the user input, whether to modify the schedule, the modification comprising at least one of: removing the health task reminder scheduled for the first day and/or time; permanently altering a day and/or time of the health task reminder; and temporarily altering a day and/or time of the health task reminder; and (vi) when it is determined to modify the schedule: storing the modified schedule; and displaying the health task reminders on the display device of the user device according to the modified schedule.

Pursuant to another exemplary embodiment of the disclosures, a computer readable apparatus is disclosed. In one embodiment, the computer readable apparatus comprises a plurality of executable instructions which are configured to, when executed by a processor: (i) store, at a storage apparatus of a user device, a schedule indicating a day and/or time for a plurality of health task reminders to be displayed to a user; (ii) display, at a display apparatus of a user device, a heath task reminder at a first day and/or time based on the schedule; (iii) receive user input relating to the health task reminder; (iv) complete the display of the health task reminder based on the user input; (v) process the user input to determine whether to modify the schedule, the modification comprising at least one of: removal of the health task reminder scheduled for the first day and/or time; and alteration of a day and/or time of the health task reminder scheduled for the first day and/or time; (vi) when it is determined to modify the schedule: storing the modified schedule; and displaying the health task reminder on a display of the electronic display device according to the modified schedule; and (vii) when it is determined not to modify the schedule, continuing display of the plurality of health task reminders according to the schedule.

In accordance with yet another exemplary embodiment, a user device is disclosed. The user device comprises: a display apparatus configured to provide a display to a user; an input apparatus configured receive inputs from the user; a storage apparatus; and a processor configured to execute at least one computer application thereon, the computer application comprising a plurality of instructions stored at the storage apparatus and which are configured to, when executed, cause the user device to: (i) store a schedule, the schedule indicating a day and/or time for each of a plurality of health task notifications to be displayed to the user; (ii) display a heath task notification at a first day and/or time based on the schedule; (iii) receive user input relating to the health task notifications; (iv) process the user input to determine whether to: (a) remove the health task notification from the first day and/or time to generate a modified schedule, (b) alter the first day and/or time of the health task notification to generate the modified schedule, or (c) make no modifications to the schedule and omitting to generate the modified schedule; (v) continuing to display the plurality of health task notifications to the user according to the modified schedule when a modified schedule is generated and according to the schedule when generation of the modified schedule is omitted.

BRIEF DESCRIPTION OF THE DRAWINGS

The foregoing aspects and other features of a health and fitness tracking system are explained in the following description, taken in connection with the accompanying drawings.

All Figures © Under Armour, Inc. 2017. All rights reserved.

DETAILED DESCRIPTION

In the following detailed description, reference is made to the accompanying figures which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Figure 1:
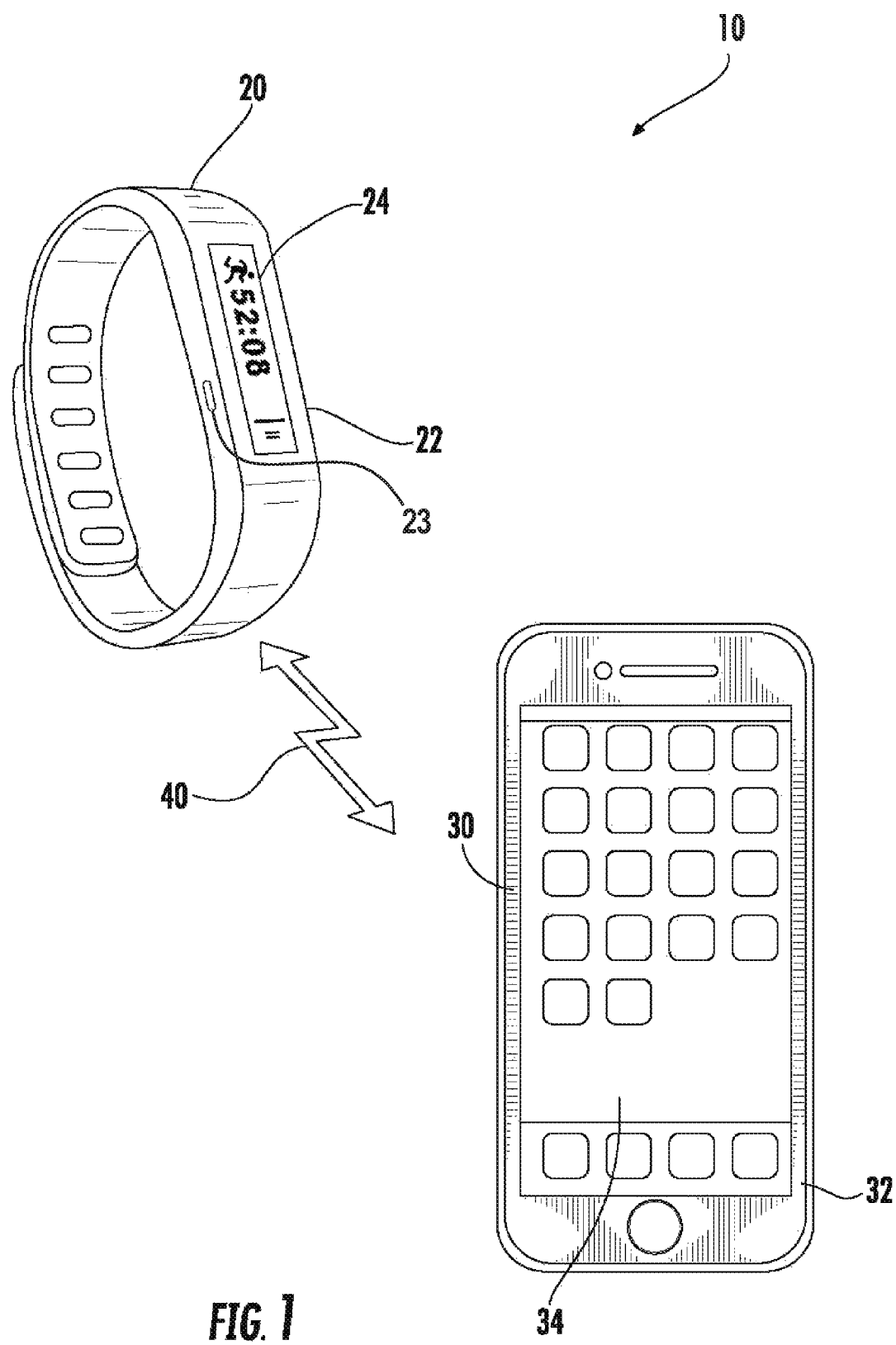
FIG. 1 is a diagrammatic view showing an exemplary embodiment of a health tracking system including a health monitoring device and an electronic display device.
Figure 2:
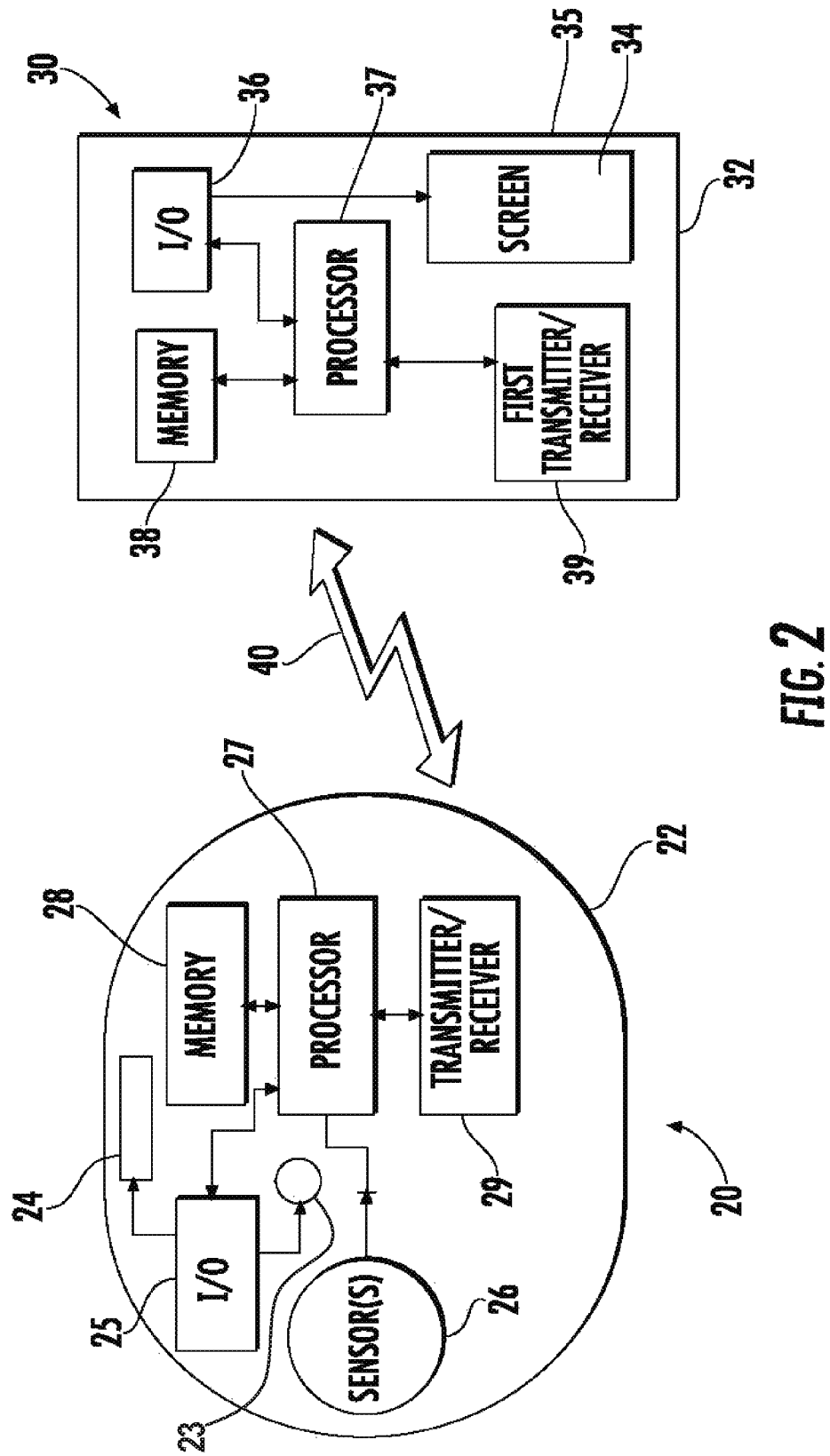
FIG. 2 is a block diagram of exemplary electronic components in the health monitoring device and the electronic display device of the health tracking system of FIG. 1.

With reference to FIGS. 1-2, an exemplary embodiment of a health tracking system 10 includes at least one health monitoring device 20 and an electronic display device 30 in communication therewith. The health monitoring device 20 is a user device configured to measure one or more health parameters of a user and provide health data to the electronic display device 30. In many embodiments, the health monitoring device 20 is designed and dimensioned to be worn on or carried by the body of a user. However, the health monitoring device 20 may also comprise a non-portable device. In some embodiments, the health tracking system 10 includes more than one health monitoring device 20 associated with the individual user. The electronic display device 30 is a user device designed to process the health data and display it to the user in a format that shows context for daily exercise, general activity, nutritional habits, and sleep behavior. In some embodiments, the electronic display device 30 may also collect health data independently of any separate health monitoring device 20 and, in this way, may function as the health monitoring device 20 or one of the health monitoring devices 20.

The term "health data" as used herein refers to data relating to a user's health and general well-being, and may also be referred to herein as "health information" or "health parameters." Health data may include activity data, nutritional data, physiological data, and health perception data. Health data may be in a raw measured form or in a processed form. Health data may be automatically measured, sensed, or collected by the health monitoring device 20 and/or the electronic display device 30, but may also be entered manually by the user via the health monitoring device 20 and/or the electronic display device 30. The term "activity data" as used herein is a subset of health data, and refers to data related to physical activity (i.e., movement or lack thereof) of the user. Examples of activity data include step data, body motion data, distance traversal data, altitude data, heart rate data, breathing data, environmental/positional data (such that provided by a GPS receiver), and/or any of various other types of personal activity metrics that may be relevant the user's physical activity for a given period of time. The term "nutritional data" as used herein is a subset of health data, and refers to data related to dietary consumption of the user. Examples of nutritional data may include dietary logs for foods and beverages consumed by the user, as well as nutritional content information such as caloric content, macronutrients, micronutrients, serving size, and/or other nutrition and health information for the foods and beverages consumed by the user. Nutritional data may also include logs and information regarding dietary supplements, vitamin supplements, medication, or any of various other items for consumption that may be relevant the user's dietary consumption for a given period of time. The term "physiological data" as used herein is a subset of health data, and refers to data related to the physiological status and health of the user. Examples of physiological data include age, gender, height, body weight, body fat, heart rate, aspiration rate, blood oxygenation, blood glucose, hydration, sleep patterns, caloric expenditure, or any of various other types of physiological metrics that may be relevant the user's physiological health for a given period of time. The term "health perception data" as used herein is a subset of health data, and refers to data related a personal feeling or subjective perception of one's own health as determined by the user himself or herself based on the user's own senses, feelings, awareness, mental impressions, and/or other perceptions of the user. Health perception data may broadly relate the user's perception of his or her overall health, but may also relate to the user's perception of particular aspects of his or her health, such as the user's perception of his or her caloric intake, weight, activity level, and/or any of the health parameters discussed above.

Although not illustrated, in one embodiment, the health monitoring device 20 and electronic display device 30 may communicate via a network to a network-side database and/or server (not shown) for storage and/or processing of the health data, thereby decreasing the processing capacity required at either user device (e.g., the health monitoring device 20 or electronic display device 30).

While the health monitoring device 20 is described herein as the primary device for collecting and transmitting health data to the electronic display device 30, it will be recognized that additional data may also be collected or otherwise obtained and/or input in to the electronic display device 30 via various other mechanisms. In at least one embodiment, the user may manually input data directly into the health monitoring device 20 and/or the electronic display device 30. For example, the user may manually collect sleep data or calorie consumption data and input such data into the health monitoring device 20 and/or the electronic display device 30 without the use of a sensor and/or other device for transmitting the health data to the electronic display device 30.

In the instance in which a user carries one or more health monitoring devices 20, health data from each device 20 is delivered to the electronic display device 30. As represented by the arrow 40 in FIGS. 1 and 2, the one or more health monitoring devices 20 are configured to transmit a wireless RF signal representative of the health data collected or obtained thereat to at least one display device 30. In addition, the health data may also be transmitted to additional computing devices, such as a watch, personal computer, and/or a laptop computer where the health data may be conveniently displayed for the user. In other embodiments, a wired connection may be utilized for communication of health data between the electronic display device 30 and the health monitoring device 20. Similarly, in another embodiment, the health data may be transmitted from the health monitoring devices 20 and/or the display device 30 to the aforementioned network server (not shown). The data may then be accessed by the user at any number of additional computerized devices via a username and password, or other form of identification and authentication of the user.

In another embodiment, the transmission of data from the health monitoring device 20 to the electronic display device 30 (or to a network server (not shown)) occurs automatically without requiring the user to prompt or initiate the transmission. Since the transmissions in this embodiment are automatic, a mechanism may be provided to turn on the transmitter/receiver 29 of the health monitoring device 20 or otherwise indicate that automatic transmissions should begin. For example, in one embodiment, an on/off switch is provided on the health monitoring device 20 that allows the athlete or user to begin automatic transmissions of data from the health monitoring device 20. In another embodiment, the health monitoring device 20 may be configured to begin transmissions once it receives a confirmation that the electronic display device 30 is within an appropriate range of the health monitoring device 20. In yet another embodiment, data transmission may occur periodically at predetermined intervals of time. In other embodiments, where communications between the health monitoring device 20 and the electronic display device 30 are made with a wired connection, communications only occur when the wired connection is established between the health monitoring device 20 and the electronic display device 30. Similar logic applies to the transmission of data from the health monitoring device 20 and/or the electronic display device 30 to the network server (not shown).

In the embodiment disclosed herein, the health monitoring device 20 is shown as being a completely separate unit from the electronic display device 30. However, in at least one embodiment, the health monitoring device 20 and the electronic display device 30 are provided as a single unit. For example, the health monitoring device 20 and the electronic display device 30 may be provided as part of a mobile phone, so-called "smart" watch or other personal electronic device. In such embodiments, duplicative hardware described below can be combined and/or eliminated. Additionally, while a single health monitoring device 20 is shown in the embodiment of FIG. 1, it will be recognized that multiple health monitoring devices 20 may be used by a single user, each of the health monitoring device 20 configured for communication with the electronic display device 30. An exemplary health monitoring device 20 and an exemplary electronic display device 30 will be discussed in further detail below.

Health Monitoring Device

With continued reference to FIGS. 1-2, the health monitoring device 20 (which may also be referred to herein as a "health tracking device", a "user device", or a "sensor device") may be provided in any of various forms and is configured to measure, collect and/or otherwise obtain any of the various types of health data (as discussed above). The health data may be collected automatically by a sensor of the health monitoring device 20, via manual entry by the user, and/or collected by any of various other means. In at least one embodiment, the health monitoring device 20 is an activity tracker configured to measure one or more of steps taken (including walking or running), distance traversed, stairs climbed, heart rate, as well as various other types of activity data or physiological data (such "activity trackers" are commonly also referred to as "fitness trackers").

In one exemplary embodiment the health monitoring device 20 is configured to be worn or carried by the human user. For example, in the embodiment shown in FIG. 1, the health monitoring device 20 is provided as a wrist band that the user straps to his or her wrist. However, it will be recognized that in other embodiments, the health monitoring device 20 may be provided in any of various different configurations to be worn on any of various locations on the body of the user, such as via a module that clips on to clothing, is worn on a chest strap, fits in a pocket of the user, and/or is incorporated into a garment or a shoe. Alternatively, the health monitoring device 20 may be fixed and non-portable device (i.e., not worn by the user), such as for example, a so-called smart scale onto which a user stands, a smart mattress pad, and/or a tablet or personal computing device into which the user enters health data, such as nutritional data. Additional examples of configurations for the health monitoring device 20 include configurations where the sensor device is provided as a component of a multi-function device, such as a watch, a mobile phone or other personal electronic device. Additional or alternative examples of health-monitoring devices 20 include those sold under the trademarks FITBIT®, JAWBONE®, POLAR®, APPLE® and UNDER ARMOUR®.

With continued reference to the embodiment of FIGS. 1 and 2, the health monitoring device 20 includes a protective outer shell or housing 22 designed to retain and protect various sensors and other electronic components positioned within the housing 22. The housing 22 comprise any number of shapes, configurations, and/or materials, the description herein being merely exemplary. In at least one embodiment, the housing 22 includes a relatively rigid portion that securely retains the electronic components, and a more resilient portion which functions as an outer layer to provide shock absorption features in the event the health monitoring device 20 is dropped, falls, or otherwise withstands an amount of force. The health monitoring device 20 and housing 22 may be configured to be worn or otherwise carried by the user in any of a number of ways. For example, the housing 22 of the health monitoring device 20 may be provided as part of a chest or wrist strap having an associated clasp, or may include a clip or other arrangement that allows the health monitoring device 20 to be coupled to the clothing of the user (as discussed elsewhere herein).

The health monitoring device 20 may also include other features visible on the housing 22 such a button 23, a display 24, one or more connection ports (not shown), or other input/output hardware and software that operate in conjunction with an I/O interface 25. In the embodiment shown, the button 23 comprises a tactile button, switch, and/or toggle. However, in other embodiments, the button 23 may also comprise capacitive or resistive touch sensor. The display 24 may vary based on the type of device. For example, in the embodiment shown, the display 24 comprises an LCD or LED screen that provides health metric information (e.g., total number of steps for the day, progress towards a goal, heart rate, some combination thereof, etc.), notifications, text messages, caller ID, etc. to the user. In some embodiments, the display 24 is a touch screen display that allows the user to provide inputs to the I/O interface 25 via virtual buttons or other interfaces on the touch screen. Alternatively, in one embodiment, the display 24 may simply be one or more colored lights and/or flashing patterns configured to communicate information to the user (e.g., progress towards a goal or other health metric). The connection ports may be used to connect the health monitoring device 20 to a power source or to share data with other electronic devices.

As shown in FIG. 2, the health monitoring device 20 includes electronic circuitry comprising, the I/O interface 25, one or more sensors 26 (optional), a processor 27, a memory 28, and the transmitter/receiver 29. The health monitoring device 20 also includes a battery or other power source (not shown) configured to power the various electronic devices within the health monitoring device 20. In at least one embodiment, the battery of the health monitoring device 20 is a rechargeable battery. In this embodiment, the health monitoring device 20 may be placed in or connected to a battery charger configured for use with the health monitoring device 20 in order to recharge the battery.

In one embodiment, the health monitoring device 20 comprises one or more sensors 26. The sensors 26 may comprise any of various devices configured to collect the activity or physiological data, including step data, motion data, distance traversal data, GPS data, body weight data, altitude data, heart rate data, body temperature data, breathing data, environmental/positional data, and/or any of various other types of health data that may be relevant to determining activities of the wearer. In at least one embodiment, the sensors 26 include a 3-axis accelerometer configured to detect the steps of the wearer during walking and running, and general movements of the wearer during more sedentary periods such as sleep. Of course, it will be recognized by those of ordinary skill in the art that numerous other sensors may be used, depending on the type of activity the health monitoring device 20 is designed to detect.

With continued reference to FIG. 2, the processor 27 may be any of various microprocessors as will be recognized by those of ordinary skill in the art. The processor 27 is configured to receive data signals from the sensors 26, and other component parts of the health monitoring device 20 (such as data entered via the I/O interface 25), and process such signals. The processor 27 is connected to the memory 28 and the transmitter/receiver 29, and may deliver processed data to one or both of the memory 28 and the transmitter/receiver 29. Additionally, the processor 27 may perform some processing on the received data prior to delivery thereof to the memory 28 or transmitter/receiver 29. For example, the processor 27 may associate the health data with a particular time, day, user (in the instance that the device is configured to collect data relating to more than one user), and/or event. The processor 27 is also connected to the I/O interface 25, and may send signals to the I/O interface 25 which results in illumination of the display 24 in order to provide text and/or image based messages or otherwise communicate to the user.

The memory 28 is configured to store information, including both data and instructions. The data may be retrieved from the processor 27 and generally includes health data, but may also include various types of operational data that may be ancillary to the basic operation of the health monitoring device 20. The instructions which are stored at the memory 28 generally include firmware and/or software for execution by the processor 27, such as a program that controls the settings for the sensor device, a program that controls the output of the display 24 on the health monitoring device 20, a program that controls the receipt of information via the sensor 26, a program that controls the transmission and reception of data via the transmitter/receiver 29, as well as any of various other programs that may be associated with the health monitoring device 20. Such instructions may be present on the device 20 at the time of manufacture or may be downloaded thereto via well-known mechanisms. The memory 28 may be of any type capable of storing information accessible by the processor 27, such as a memory card, ROM, RAM, write-capable, read-only memories, or other computer-readable medium. The data may be stored in the memory 28 in a relational database as a table having a plurality of different fields and records, XML documents, or flat files. The data may also be formatted in any computer-readable format such as, but not limited to, binary values, ASCII or Unicode.

The transmitter/receiver 29 in one embodiment comprises an RF transmitter and receiver configured to transmit and receive communications signals over a short range using a wireless communications technology, such as Wi-Fi or Bluetooth®, using any of various communications protocols, such as TCP/IP. Such transmitter/receivers are well known and will be recognized by those of ordinary skill in the art. The transmitter/receiver 29 is particularly configured to communicate with the electronic display device 30 when the health monitoring device 20 is within a given range of the electronic display device 30, and transmit collected health data to the electronic display device 30.

Electronic Display Device

With continued reference to FIGS. 1-2, the electronic display device 30 (also referred to herein as a "user device") generally includes an input/output interface 36, a processor 37, a memory 38, and a transmitter/receiver 39. Additionally, the electronic display device 30 also includes a battery or other power source (not shown) configured to power the electronic components within the electronic display device 30. In at least one embodiment, the electronic display device 30 is a handheld computing device, such as a smartphone. While a smartphone has been shown as the electronic display device 30 in FIGS. 1 and 2, it will be appreciated that the electronic display device 30 may alternatively comprise any number of devices. For example, the electronic display device 30 may be a standalone device, such as a desktop PC, and/or smart television. Alternatively, the electronic display device 30 may be any type of portable or other personal electronic device such as a watch, tablet computer, laptop computer, and/or any of various other mobile computing devices. As will be recognized by those of ordinary skill in the art, the components of the electronic display device 30 may vary depending on the type of display device used. Such alternative display devices may include much (but not necessarily all) of the same functionality and components as the electronic display device 30 shown in FIGS. 1 and 2, as well as additional functionality or components necessary for proper functioning thereof (not shown).

The I/O interface 36 of the electronic display device 30 includes software and hardware configured to facilitate communications with the one or more health monitoring devices 20 and/or communications to the user him/herself. The hardware includes a display screen 34 configured to visually display graphics, text, and other data to the user. The hardware may also include a microphone and/or speakers to facilitate audio communications with the user and/or verbal entry of commands to the device 30. In at least one embodiment, the display screen 34 is a touch screen display that allows the user to see data presented on the display screen 34 and input data into the electronic display device 30 via a virtual keyboard or other interface on the touch screen. However, other means for receiving user input, such as a physical keyboard, may also be provided with equal success.

The processor 37 of the electronic display device 30 may be any of various processors as will be recognized by those of ordinary skill in the art. The processor 37 is connected to the I/O interface 36, the memory 38, and the transmitter/receiver 39, and is configured to deliver data to and/or receive data from each of these components. It will be recognized by those of ordinary skill in the art that a "processor" as used herein includes any hardware system, hardware mechanism or hardware component that processes data, signals, and/or other information. A processor can include a system with a central processing unit, multiple processing units, dedicated circuitry for achieving functionality, and/or other systems.

The memory 38 is configured to store information, including both data and instructions. The data may be, for example, health data as discussed above, which may be related to the activities, nutrition, sleep, environment, etc. of the user, along with other operational data that may be ancillary to the basic operation of the electronic display device 30 and any applications retained on the electronic display device 30. The instructions which are stored at the memory 38 generally include firmware, an operating system, and/or other software for execution by the processor 37, such as one or more programs that control the settings for the electronic display device, one or more programs that control the output of the display 34 on the electronic display device 30, one or more programs that control various applications on the electronic display device 30, one or more programs that control the transmission and reception of data via the transmitter/receiver 39, as well as any of various other programs that may be associated with the electronic display device 30. In at least one embodiment, the instructions stored in the memory 38 include activity or health tracking application, discussed in greater detail below, which is executed by the processor 37 to process health data and present the health data in a graphical format on the display screen 34. The memory 38 may be of any type of device capable of storing information accessible by the processor, such as a memory card, ROM, RAM, write-capable memories, read-only memories, hard drives, discs, flash memory, or any of various other computer-readable medium serving as data storage devices, as will be recognized by those of ordinary skill in the art.

The transmitter/receiver 39 is, in one embodiment, an RF transmitter and receiver configured to transmit and receive communications signals using a wireless communications technology, such as Wi-Fi or Bluetooth®, using any of various communications protocols, such as TCP/IP. Such transmitter/receivers are well known and will be recognized by those of ordinary skill in the art. The transmitter/receiver 39 is particularly configured to communicate with a transmitter/receiver 29 of the health monitoring device 20. In at least one embodiment, the transmitter/receiver 39 is configured to allow the electronic display device 30 to communicate with a wireless telephony network, as will be recognized by those of ordinary skill in the art. The wireless telephony network may comprise any of several known or future network types. For example, the wireless telephony network may comprise commonly used cellular phone networks using CDMA or FDMA communications schemes. Some other examples of currently known wireless telephony networks include Wi-Fi, WiMax, GSM networks, as well as various other current or future wireless telecommunications arrangements.

The electronic display device 30 generally includes a protective outer shell or housing 32 designed to retain and protect the electronic components positioned within the housing 32. The housing 32 may comprise any number of shapes, configurations, and/or materials, the description herein being merely exemplary. In at least one embodiment, the housing 32 includes a relatively rigid portion that securely retains the electronic components, and a more resilient portion which functions as an outer layer to provide shock absorption features in the event the device 30 is dropped, falls, or otherwise withstands an amount of force. In embodiments wherein the electronic display device 30 also functions as one of the health monitoring devices 20, the housing 32 may serve as a common housing for components of the electronic display device 30 and components of the health monitoring device 20.

In at least one embodiment, the instructions stored in the memory 38 of the electronic display device 30 includes an activity or health tracking application (which may also be referred to herein as the "health tracking application"), which is executed by the processor 37 to provide a graphical user interface that enables the user to view and manage his or her health data. An exemplary health tracking application will be discussed in further detail below.

Health Tracking Application

In one exemplary embodiment, the health tracking application at least includes instructions for processing health data and presenting the health data in a graphical format to a user (such as on the display screen 34 of the electronic device 30). Additionally, in one embodiment, the health tracking application includes features that enable the user to set and manage his or her health and fitness goals. Furthermore, in one embodiment, the health tracking application includes coaching features, discussed in greater detail below, designed to encourage and guide the user in achieving his or her desired health and fitness goals.

Typical processing of the health data may relate to the user's current activity level, trends, history, training state, etc. For example, in one embodiment the one or more computers that processes the raw data may calculate an activity level which may be based on a combination of inputs, including, for example, steps taken over a period of time, heart rate, etc. In another embodiment, GPS data is used to determine various athletic data points, such as the speed of the athlete calculated over different time periods, total distance travelled, or the route taken by the athlete (such as during a sporting event).

In many embodiments, the health data transmitted to the electronic display device 30 is processed to determine one or more health metrics for the user. The term "health metric" as used herein refers to any standard of measurement relevant to an assessment of the health and general well-being of the user. Health metrics can be considered a type of health data. In some cases, the raw measured health data is processed substantially to provide a health metric, but in other cases, measured health data may simply be organized into a more presentable form to provide the health metric. Some examples of health metrics include heart rate data expressed as beats per minute, activity data expressed a number of steps for a day, activity data expressed as a distance traversed over some time period, a number of calories spent over some time period, a number of calories consumed for a day, a total duration of activity, a body weight, an amount of body fat, and sleep quality defined by sleep time and/or sleep quality/sleep cycles. Many of the health metrics are directly associated with health and fitness goals set by the user. Further exemplary health metrics may include any parameter of health data expressed as a number or as a percentage of a user's health or fitness goal or other standard.

In some embodiments, activity data may be processed to determine an activity level of the user. Particularly, if the activity data indicates that the user is walking or running, the processor 37 may determine that the user is participating in a high intensity awake activity and/or may calculate a value for the intensity level. On the other hand, if the activity data indicates that the user is sitting or generally sedentary, the processor 37 may determine that the user is participating in a lower level awake activity. In at least one embodiment, the activity data may indicate that the user is sleeping or has retired to bed for an evening. In another embodiment, the user may indicate on the health monitoring device 20 and/or on the electronic display device 30 that he or she has retired to bed (e.g., by making an appropriate selection on the device 20 or 30). During these times, the processor 37 may determine a quality of sleep of the user by determining activity levels during sleep. Relatively low movement and/or low heart rate during sleep may indicate deeper sleep levels and significant movement during sleep and/or increased heart rate may indicate lighter sleep or even additional awake times. When the user awakens the following morning, the processor 37 may automatically determine based on the activity signals that the user has awakened from his or her sleep and is participating in activities of various intensities.

In some embodiments, processing of health data may also depend on a subscription level the user maintains with the administrator of the health tracking system 10. If the user has a standard subscription with the administrator of the health tracking system 10, only limited processing may occur, such as an average heart rate for a period of time or a total number of steps for a day. However, if the user has a higher subscription level with the administrator of the health tracking system, the processing of heart rate data may further include an analysis of the time the user spent in different heart rate zones during a given period of time, such as times in the fat burning zone, the aerobic zone, and the anaerobic zone. With respect to step data, users with a higher subscription level than other users may receive access to detailed information about cadence, split times, or other in-depth analysis performed by the processor (which is not available to users with standard subscription levels).

While these are but a few examples of how the raw data may be processed by one or more computers of the health tracking system including the electronic display device 30 or any remote servers, those of skill in the art will recognize that nearly countless other possibilities exist for systems and methods to process the data received from the one or more health monitoring devices 20 for subsequent viewing and analysis. Furthermore, the health data may be processed into different forms and formats, depending on the particular device that will ultimately be used to view the data. For example, the data may be processed into a first format that is a compressed or summarized format that will allow it to be viewed on as smaller display (e.g., a smart watch) and into a second format that is a more detailed format that will allow it to be viewed on a more powerful display (e.g., the monitor of a personal or laptop computer).

After the health data is processed, it is displayed on the display screen 34 or otherwise presented on a user interface of the electronic display device 30 (or other device). To this end, the processor is configured to communicate with the I/O interface 36 and cause display of the processed health data on the screen 34 for viewing by the user.

In at least one embodiment, portions of the system and methods described herein may be implemented in suitable software code that may reside within the memory. Such software code may be present on the device 30 at the time of manufacture or may be downloaded thereto via well-known mechanisms. A computer program product implementing an embodiment disclosed herein may therefore comprise one or more computer-readable storage media storing computer instructions translatable by a processor to provide an embodiment of a system or perform an embodiment of a method disclosed herein. Computer instructions may be provided by lines of code in any of various languages as will be recognized by those of ordinary skill in the art. A "computer-readable medium" may be any type of data storage medium that can store computer instructions, including, but not limited to the memory devices discussed above.

In another embodiment, a permanent copy of the programming instructions for individual ones of the aforementioned applications (e.g., the health tracking application) may be placed into permanent storage devices (such as e.g., memory 28 and/or memory 38) during manufacture thereof, or in the field, through e.g., a distribution medium (not shown), such as a compact disc (CD), or through transmitter/receiver 29 and/or transmitter/receiver 39 (from a distribution server (not shown)). That is, one or more distribution media having an implementation of the agent program may be employed to distribute the agent and program various computing devices.

Coaching Features of the Health Tracking Application

In at least one embodiment, the health tracking application includes coaching features designed to encourage and guide the user in achieving his or her desired health and fitness goals. In particular, the health tracking application contains in instructions for providing health task notifications. The term "health task notifications" (which may also be referred to herein as "plays") as used herein refers to messages, notifications, and/or reminders that are displayed, presented, or otherwise provided, to a user that relate to a particular a health or fitness task or topic. The terms "health task" and "fitness task" as used herein refer to any action that can be performed by the user and relates to his or her health and/or fitness. Examples of health and fitness tasks may include going to bed, taking a walk, tracking a workout, logging a meal, setting a health or fitness goal, getting weighed, and/or any scheduling or planning of future tasks relating to his or her health and/or fitness.

In at least one embodiment, health task notifications include a message to the user that provides actionable recommendations, guidance, encouragement, and/or insights relating to a health or fitness task. In some embodiments, health task notifications may include a reminder or call to action for the user to perform a particular health or fitness task. Such health task notifications may include, for example, a reminder to go to bed, a reminder to log nutrition for the day, a suggestion to track a work out, and/or a suggestion to take a walk. Additionally, in some embodiments, health task notifications may include suggestions to set or manage a health and fitness goal. Such health task notifications may include, for example, a suggestion to set a bedtime reminder, a suggestion to create a meal plan or schedule, and/or a suggestion to create a workout plan or schedule. However, not all health task notifications comprise a specific call to action for the user to perform a health or fitness task. Instead, in some embodiments, health task notifications may include general insights, tips, and guidance relating to nutrition, sleep, exercising, and/or other health and fitness tasks or topics.

Figure 3:
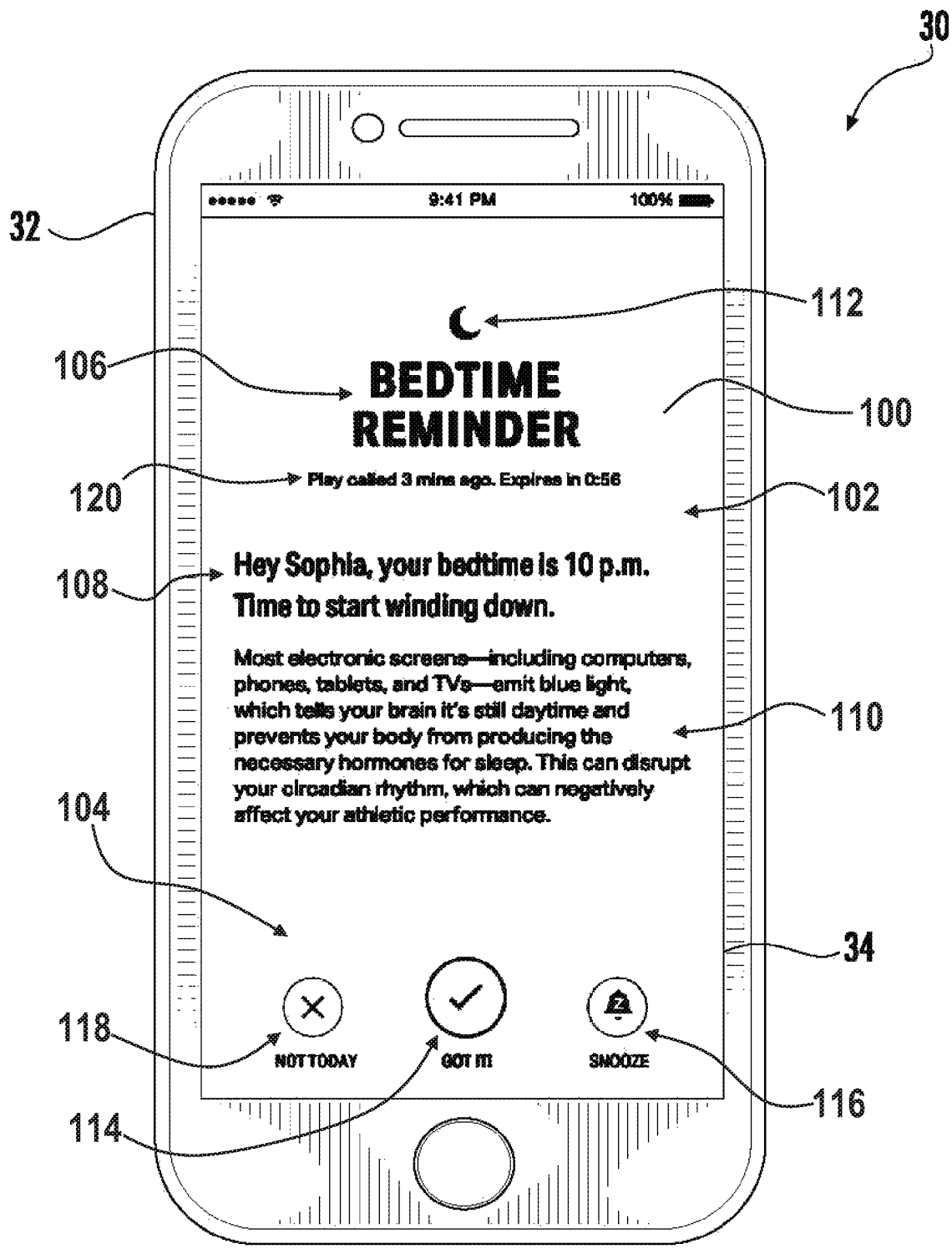
FIG. 3 is a plan view showing the electronic display device of the health tracking system of FIG. 1 displaying a health task notification screen.

FIG. 3 shows an exemplary embodiment of a health task notification screen 100 that is displayed on the display screen 34 of the user device 30 to provide a health task notification (i.e. a "play") to the user. Particularly, the processor 37 executes instructions of the health tracking application stored in the memory 38 to display the health task notification screen 100 on the display screen 34 at a first day and/or time according to a schedule. As noted elsewhere herein, the user may be prompted to create the schedule for displaying certain messages when he/she establishes a health goal and/or a default schedule may be provided based on the user's goals. The schedule and/or modifications thereto are entered via inputs to the user device 30. The default schedule may be modifiable by the user directly and/or via patterns of behavior learned from user interactions (as discussed below). The health task notification screen 100 at least includes a message 102 and a prompt 104 that enables the user to provide an input in response to the message 102. In the embodiment shown, the message 102 of health task notification screen 100 includes a title 106 (e.g., "Bedtime Reminder") which identifies the nature of the particular play that is provided by the health task notification screen 100 (e.g., a reminder to go to bed at a previously scheduled bedtime). Additionally, the message 102 of the health task notification screen 100 may include a summary 108 (e.g. "Hey Sophia, your bedtime is 10 p.m. Time to start winding down.") which conveys the content of the particular play, and which generally includes a recommendation to perform a particular health task as well as additional information relating to the task (e.g., to prepare to go to bed by 10 p.m.). Finally, the message 102 of the health notification screen 100 optionally includes detailed guidance 110 which provides additional information and context to the user about the health and fitness benefits of performing the recommended health task (e.g., "Most electronic screens—including computers, phones, tablets, and TVs—emit blue light which tells your brain it's still daytime and prevents your body from producing the necessary hormones for sleep. This can disrupt your circadian rhythm, which can negatively affect your athletic performance."). In the embodiment shown, the message 102 of the health notification screen 100 further includes an icon 112. The icon 112 is generally indicative of the health or fitness topic about which the play pertains (e.g., a crescent moon icon is used for sleep related plays). It is appreciated that as referred to herein, the health task notification may include any of the messages illustrated including e.g., the message 102, the summary 108, and the detailed guidance 110, as well as any combination thereof.

As mentioned above, the health task notification screen 100 also includes a prompt 104 that enables the user to provide an input in response to the message 102. In the illustrated embodiment, the prompt 104 includes at least three options that are selectable by the user to provide an input in response to the message 102. In the embodiment shown, the prompt 104 includes an acceptance option 114 (e.g., "Got It!") indicating that the user accepts the play, a delaying option 116 (e.g., "Snooze") indicating that the user wants to receive the message at a later time, and a dismissal option 118 (e.g., "Not Today") indicating that the user does not want to accept the play today. In response to the user pressing one of the options 114, 116, 118 on the screen 34, the I/O interface 36 is configured to provide the selection of the user to the processor 37 and/or the processor 37 is configured to determine which of the options 114, 116, 118 was selected based on input information received from the I/O interface 36.

In one embodiment, the processor 37 is configured to store a log of when plays are provided to a user and which of the options 114, 116, 118, if any, were selected by the user. This log is used, as discussed elsewhere herein, to determine whether changes are needed to the schedule. The user's input is further used to complete the display of the message, the completion is determined by the specific input as discussed below, and may include removal of the message from the display permanently, for a designated time (i.e., temporarily), and/or until the next scheduled iteration.

In a first example, in response the user selecting the acceptance option 114 (e.g., "Got It!"), the processor 37 is configured to generate and/or modify health data for the user to indicate that the user has accepted the play. For example, with respect to the particular play of the health task notification screen 100, in response to the user selecting the option 114, the processor 37 is configured to record health data indicating that the user has accepted the play to prepare for and go to bed by 10 p.m. This information may be used, in one embodiment, by the processor 37 to identify whether the same message or a similar message should be provided in the future. In other words, when the user accepts the health task notification message, it is an indication that the content of the message is appropriate for the user.

In another embodiment, the processor 37 is configured to monitor whether the user actually follows through with performance of the health task discussed in the notification message. Particularly, in one embodiment, the processor 37 is configured to receive activity data from the health monitoring device 20 or from a sensor of the electronic display device 30. Based on the received activity data, the processor 37 is configured to determine whether the user has actually performed the health task. In one specific example, the activity data may comprise movement, heart rate, and/or noise data which indicates whether the user has gone to bed by the time which would be necessary to meet the user's sleep goal. In another example, the activity data may comprise heart rate and/or step data which indicates that the user has begun an activity or a workout as would be necessary to meet the user's activity or workout goal for the day. It is appreciated that any type of data may be collected via the herein disclosed sensor devices and any combination of types of data may be used to determine whether the user has completed the health task, the foregoing being merely exemplary.

In another embodiment, the processor 37 is configured to record further data regarding whether the user has followed through with performing the health task and/or how long it took for the user to follow through with the health task. The user's completion of the health task is then recorded as the user's progress toward a goal. Lastly, in response the user selecting the acceptance option 114 (e.g., "Got It!"), the processor 37 may be further configured to remove the health task notification from the display screen 34 at least until the next day and/or time identified for display of the message according to the schedule.

In another example, in response the user selecting the option to delay the notification 116 (e.g., "Snooze"), the processor 37 is configured to temporarily reschedule the health task notification to be re-shown at a later time, the timing for re-displaying (i.e., delay time) may be a predetermined or alternatively the user may set the delay time. For example, with respect to the particular play of the health task notification screen 100, in response to the user selecting the delay option 116, the processor 37 is configured to modify the schedule to indicate that the bedtime reminder notifications will be sent at the delayed time. However, at the next scheduled iteration for display of the message (i.e., the next day) the temporary delay may be removed. Information relating to the selection of the delay option 116 may be used, in one embodiment, by the processor to identify whether the timing of the message should be permanently adjusted to the delay time. The same health task notification is provided to the user at the delayed time at each instance the user selects the delay option 116. In one variant, the system maintains a count with respect to the number of times the user has selected the delay option 116 and based on the count may determine when a threshold number of delays have been initiated, to stop providing the health task notification and/or to permanently change the schedule with regard to the display of the health task notification at the original date and/or time thereof.

In another embodiment, in response the user selecting the dismissal option 118 (e.g., "Not Today"), the processor 37 is configured to move, delete, or cancel the health task notification from the schedule, or otherwise mark the health task notification as ignored for the 24 hour period. In one further embodiment, based on the selection of the dismissal option 118, the processor 37 is configured to modify the schedule to remove, delete, or cancel the particular health task notification, or otherwise mark the play as ignored based on a pattern of behavior of the user with respect to the message. That is, when it is determined that the user input comprises a dismissal a threshold number of times for a particular health task notification (e.g., the bedtime reminder on Friday night), then the system may derive from that pattern of behavior that the health task notifications not should be provided on Friday nights. In other embodiments, in response the user selecting the dismissal option 118 (e.g., "Not Today"), the processor 37 is configured to simply dismiss the play from the display screen 34, and does not necessarily take any actions to modify the stored schedule. In a further embodiment, in response the user selecting the option 118 (e.g., "Not Today"), the processor 37 is configured to record health data from the user device 20 indicating that the user has not accepted and/or ignored the play to prepare for and go to bed by 10 p.m.

In either case, the processor 37 is configured to proceed with the next scheduled play at the next scheduled time. For example, if a user selects the option 118 (e.g., "Not Today") in response to a bedtime reminder on a Tuesday night, the processor 37 is configured to proceed with displaying the next scheduled bedtime reminder at the next scheduled time (e.g., on Wednesday night, if the user has only set a bedtime schedule for weeknights).

Additionally, data relating to the content of the message may be examined by the system in the instance the user frequently dismisses a particular message. The system may thereby determine that the message tone or content is not applicable or effective with regard to this user and may therefore select substitute content instead. Further, the system may receive data from the health monitoring devices 20 which indicates whether, despite the dismissal of the notification, the user met his health goal. For example, the health monitoring devices may provide data relating to an amount of steps the user took, heart rate activity indicative of a workout, and/or other data indicative of the user's sleeping pattern. The processor 37 uses this data when selecting subsequent messages aligned with a specific health goal. In other words, when the user dismisses a health task reminder relating to sleep, and then further data is obtained indicating that the user did not meet his/her sleep goal, the next scheduled sleep notification may be selected to comprise content that unites the user's dismissal with the missed sleep goal.

As discussed above, the processor 37 may be configured to store data in the memory 38, in the form of a log or similar means, indicating which of the options 114, 116, 118 is selected in response to each time the health task notification screen 100 is displayed to the user. In each instance, the stored data indicates whether user has (i) accepted the respective bedtime reminder by selecting the acceptance option 114 (e.g., "Got it!"), (ii) delayed the respective bedtime reminder by selecting the delaying option 116 (e.g., "Snooze"), and/or (iii) rejected the respective bedtime reminder by selecting the dismissal option 118 (e.g., "Not Today"). In one embodiment, the processor 37 is configured to perform analysis on the stored data indicating which of the options 114, 116, 118 is selected, and determine patterns, trends and/or insights regarding user responses. In one embodiment, the processor 37 is configured to modify a schedule for the messages based on stored data indicating which of the options 114, 116, 118 was selected at each instance it is presented and the determined trends or insights regarding user responses. The trends or insights may be related to the messages timing, content, tone, length, and/or any combination thereof. In such instance, the system may further provide a mechanism for counting the number of instances a notification on a particular day and/or time is accepted, delayed and/or dismissed as well as to store threshold values for each. These counts may be used, as discussed elsewhere herein, to determine whether a threshold is met and/or exceeded, and therefore inform whether permanent changes to a schedule or to a message's content, tone, length, etc. should be made.

It is appreciated that the aforementioned processing may be performed at a network server (not shown), then the processing results may be shared with the display device 30. Thereby easing the processing load at the display device 30.

Therefore, the foregoing coaching system advantageously enables a user to receive messages which are known to be effective by examining the user's acceptance, dismissal and/or delay and removing ineffective messages; the system further ensures that the messages are received on days and/or times which are determined to encourage the user to complete the health task by examining the user's acceptance, dismissal and/or delay and adjusting the schedule based thereon.

Exemplary Coaching Interfaces

Figure 4:
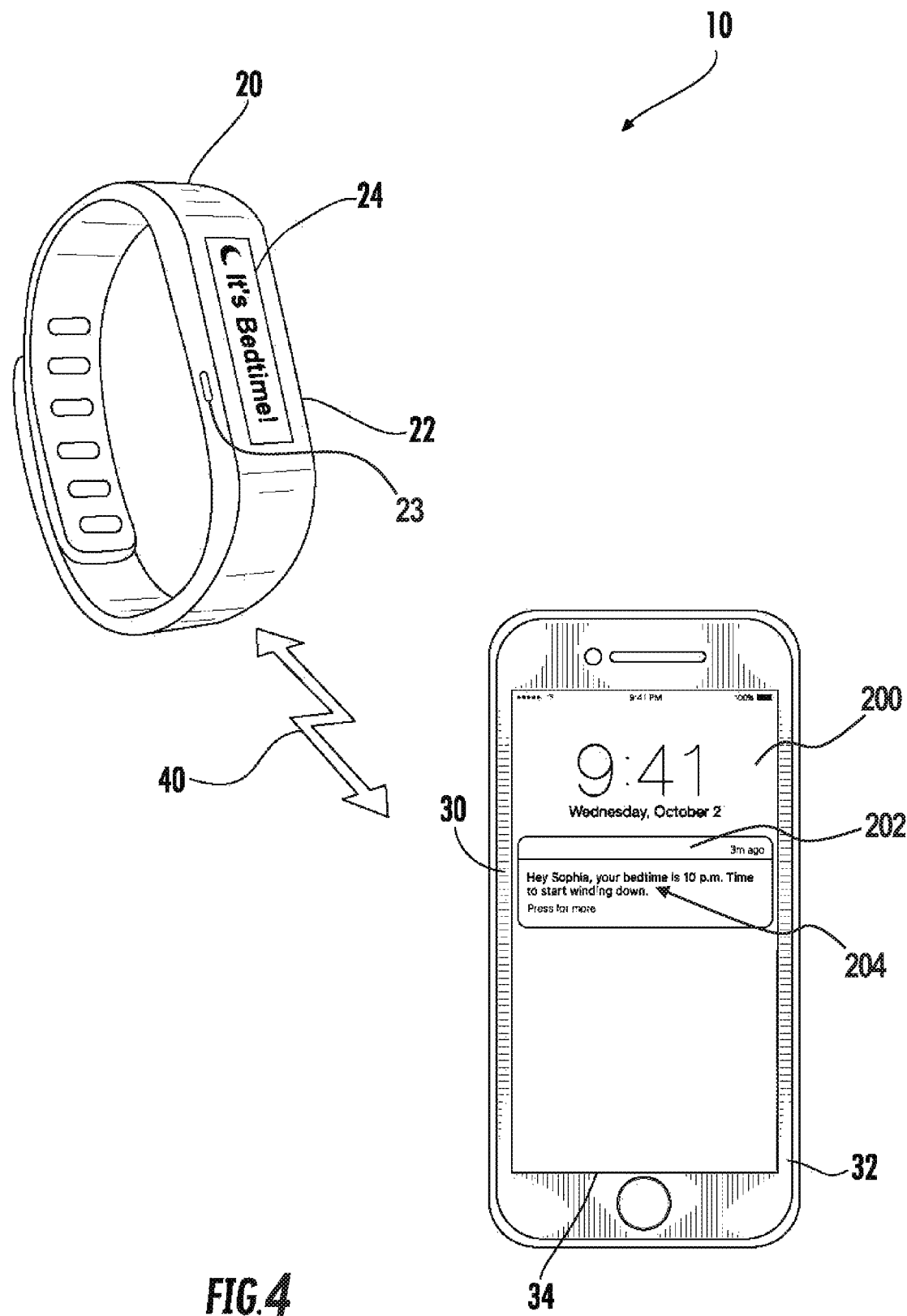
FIG. 4 is a diagrammatic view of the health tracking system of FIG. 1 illustrating health task notifications presented to a user on a display of the health monitoring device and on a lock screen of the electronic display device.

FIG. 4 shows an exemplary embodiment of how health task notifications are presented to a user by the health tracking system 10 (i.e., user interfaces). In many embodiments, the operating system of the electronic display device 30, which may be stored in the memory 38, is configured to display a lock screen on the display 34 if the electronic display device 30 has been idle for a predetermined amount of time and/or if the user interacts with the electronic display device 30 after it has been idle for a predetermined amount of time. In some embodiments, the user must enter a passcode or scan his or her fingerprint or iris in order to unlock the electronic display device 30 and dismiss the lock screen.

In at least one embodiment, the operating system of the electronic display 30 is configured to display notifications on the lock screen that are sent from the operating system or other applications stored in the memory 38. These display notifications may be the previously discussed summarized or abbreviated versions of the health task notifications/messages which are ordinarily provided to the user at the specific time. Particularly, FIG. 4 shows a lock screen 200 that is displayed on the display screen 34 of the electronic display device 30. The lock screen 200 includes health task notification 202, which was sent from the health tracking application. As shown, the health task notification 202 corresponds to the same play provided by the health task notification screen 100, discussed above. In the illustrated embodiment, the health task notification 202 includes a summary 204 (e.g. "Hey Sophia, your bedtime is 10 p.m. Time to start winding down.") that conveys the content of a particular play, which generally includes a recommendation to perform a particular health task (e.g., to prepare to go to bed by 10 p.m.). In one embodiment, the text of the summary 204 corresponds to the text of the summary 108 of the full health task notification screen 100, discussed above. It is appreciated that the content of the message may be related to any of the health tasks discussed herein, the foregoing being merely illustrative of the overall concepts.

In one embodiment of the health tracking system 10, the health monitoring device 20 is also configured to display a modified version of the health task notification to the user (such as the summarized version or other even further condensed version). Particularly, in one embodiment, the processor 37 of the electronic display device 30 is configured to operate the transmitter/receiver 39 to transmit a signal to the health tracking device 20 indicating that the health task notification should be displayed to the user via the health tracking device 20. The processor 27 of the health tracking device 20 is configured to receive the signal from the electronic display device 30 via the transmitter/receiver 29. In response to receiving the signal, the processor 27 is configured to operate the I/O interface 35 to display a message 206 on the display 24. The message 206 may be the same as the summary 204, or may be more compact and abbreviated message (e.g., "It's Bedtime!"), as shown.

In at least one embodiment, the health monitoring device 20 is configured to receive an input from the user indicating a response to the health task notification (i.e. the message 206). This may be accomplished in a manner similar to the user input into the electronic display device 30 (i.e., via selection of one of a set of icons). In another example, the user can press the button 23 one or more times and/or, in the instance that the display 24 is a touch screen, interact with the display 24 to provide a response to the health task notification. In one exemplary embodiment, the user can press the button 23 a first number of times (e.g., once) to accept the play associated with the health task notification (which is generally similar to selecting the acceptance option 114 of the health task notification screen 100). The user can press the button 23 a second number of times (e.g., twice) to snooze the play associated with the health task notification (which is generally similar to selecting the delay option 116 of the health task notification screen 100). Finally, the user can press the button 23 a third number of times (e.g., three times) to ignore/reject the play associated with the health task notification (which is generally similar to selecting the dismiss option 118 of the health task notification screen 100). As the user presses the button 23 once, twice and three times, a corresponding identifier may be provided (e.g., accept, delay, decline, etc.) and a further confirmation of the selection may be required. However, any other scheme can be utilized for inputting a selection to the health monitoring device 20.

In response to the user inputs via the button 23, the screen 24, or other inputs, the processor 27 is configured to operate the transmitter/receiver 29 transmit a signal to the electronic display device 30 which indicates the option selected by the user. The processor 37 of the electronic display device 30 is configured to receive the signal from the health monitoring device 20 via the transmitter/receiver 39. In response the receiving the signal from the health monitoring device 20, the processor 37 is configured to perform the necessary actions for the indicated selection, as discussed above with respect the options 114, 116, and 118 of the health task notification screen 100.

Figure 5:
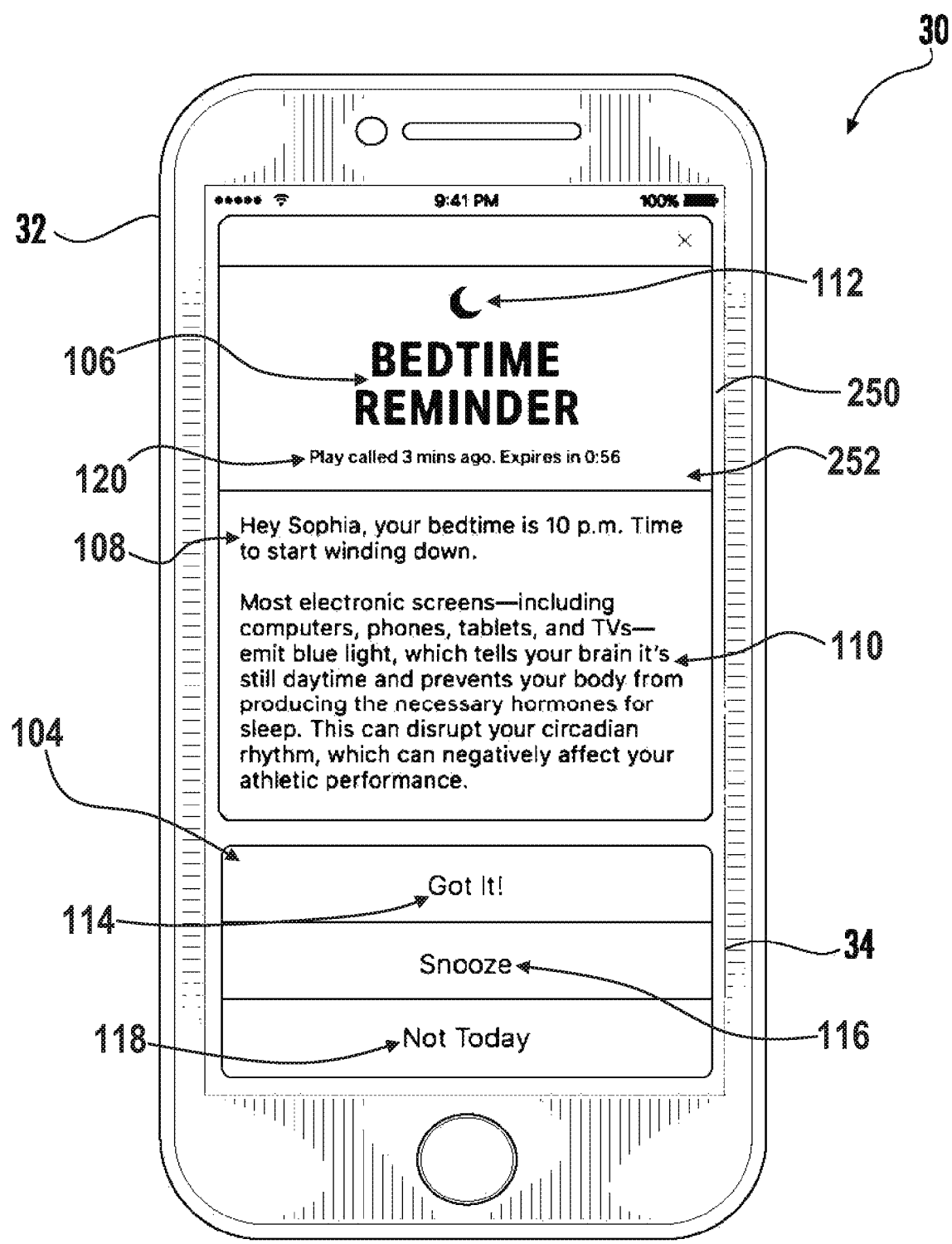
FIG. 5 is a plan view showing the electronic display device of the health tracking system of FIG. 1 displaying an expanded health task notification on the lock screen.

In another embodiment, whenever a health task notification is provided to a user via the health monitoring device 20 and/or via the lock screen of the electronic display device 30, as discussed with respect to FIG. 4, the user can interact with the electronic display device 30 to expand the health task notification 202 of the lock screen 200. In one embodiment, the user can tap, swipe, long press, deep press, or perform some other gesture using the touch screen 34 in order to expand the health task notification 202. FIG. 5 shows an exemplary lock screen 250 having an expanded health task notification 302. The expanded health task notification 252 includes essentially equivalent features as those of the health task notification screen 100 of FIG. 3 and corresponding elements of the expanded health task notification 252 are labeled using the same reference labels as in FIG. 3. The user can interact with the options 114, 116, and 118 in the same way described above with respect to FIG. 3. The primary difference between the expanded health task notification 252 and the health task notification screen 100 of FIG. 3 is that the expanded health task notification 252 is accessible via lock screen of the electronic display device 30, without unlocking the electronic display device 30.

Additionally, whenever a health task notification is provided to a user via the health monitoring device 20 and/or via the lock screen of the electronic display device 30, as discussed with respect to FIG. 4, the user can interact with the electronic display device 30 to dismiss the lock screen 200. In one embodiment, when the lock screen 200 is dismissed, the user may be automatically presented with a health task notification screen, such as the health task notification screen 100 shown in FIG. 3. Alternatively, when the lock screen is dismissed, the user may be presented with a home screen or dashboard of the operating system of the electronic display device 30 and may navigate using known methods to open the health tracking application. Once the user opens the health tracking application, he or she may be presented with a health task notification screen, such as the health task notification screen 100 shown in FIG. 3.

In some embodiments, the health task notifications provided by the health tracking application have a limited time during which the play can be accepted, or snoozed. Particularly, in one embodiment, the plays are configured to expire after a predetermined amount of time. Referring back to FIG. 3, the health task notification screen 100 further includes an expiration timer 120 that indicates when the play will expire. In one embodiment, the expiration timer 120 includes a message that indicates when the play was first sent and when the play expires (e.g., "Play called 3 mins ago. Expires in 0:56"). In one embodiment, the predetermined amount of time after which a play expires is different depending on the nature of the play (e.g., 4 minutes for a bedtime reminder, 2 hours for a recommendation to log a meal, 24 hours for a recommendation to track a workout etc.).

Figure 6:
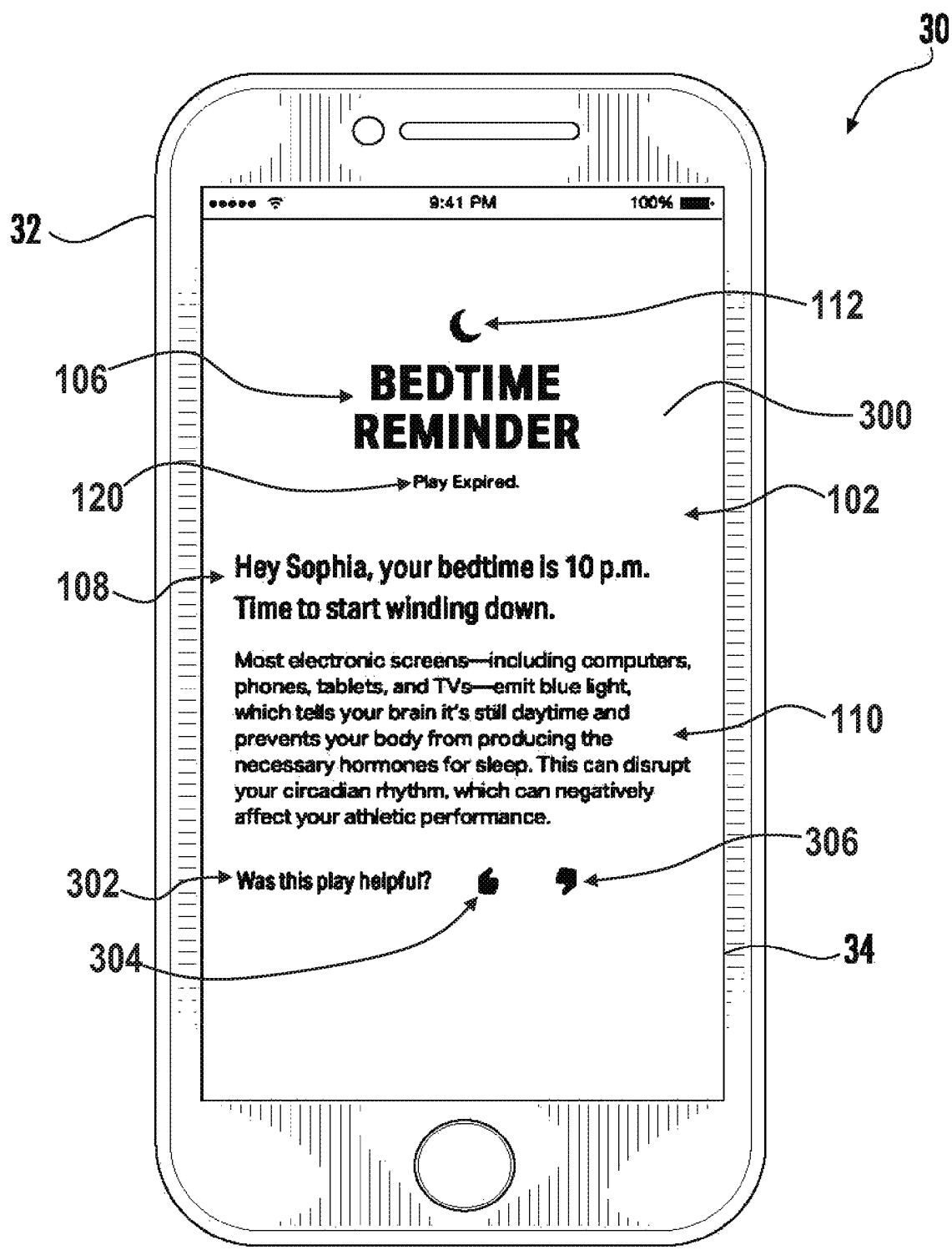
FIG. 6 is a plan view showing the electronic display device of the health tracking system of FIG. 1 displaying an expired health task notification screen.

FIG. 6 shows an exemplary embodiment of a health task notification screen 300 that is displayed on the display screen 34 of the electronic display device 30 for a play that has expired. The text of the expiration timer 120 has been updated to indicate that the play has expired (e.g. "Play Expired"). Additionally, as can be seen, the options 114, 116, and 118 of the health task notification screen 100 shown in FIG. 3 have been disabled, omitted, and/or removed. Particularly, once a play has expired, the processor 37 is configured to disable the options 114, 116, and 118 of the health task notification screen 100 shown in FIG. 3, thereby preventing the user for accepting or snoozing the play. In one embodiment, if a play expires, the processor 37 is configured to treat the play as if it was rejected or ignored, and take the same steps discussed above with respect to selection of the dismissal option 118 (e.g., "Not Today").

In another embodiment, the health task notification screen 300 includes a feedback prompt 302 (e.g., "Was this play helpful?") having selectable options for receiving feedback about the notification or message (e.g., thumbs up icon 304 and thumbs down icon 306). Accordingly, the user can provide subjective feedback about the health task notification. In one embodiment, the processor 37 is configured to store the subjective feedback in the memory 38 and/or operate the transmitter/receiver 39 to transmit the subjective feedback to a remote server (not shown) associated with the health tracking system 10, for processing thereat to determine patterns and/or modify future messages based on the feedback, etc.

Figure 7:
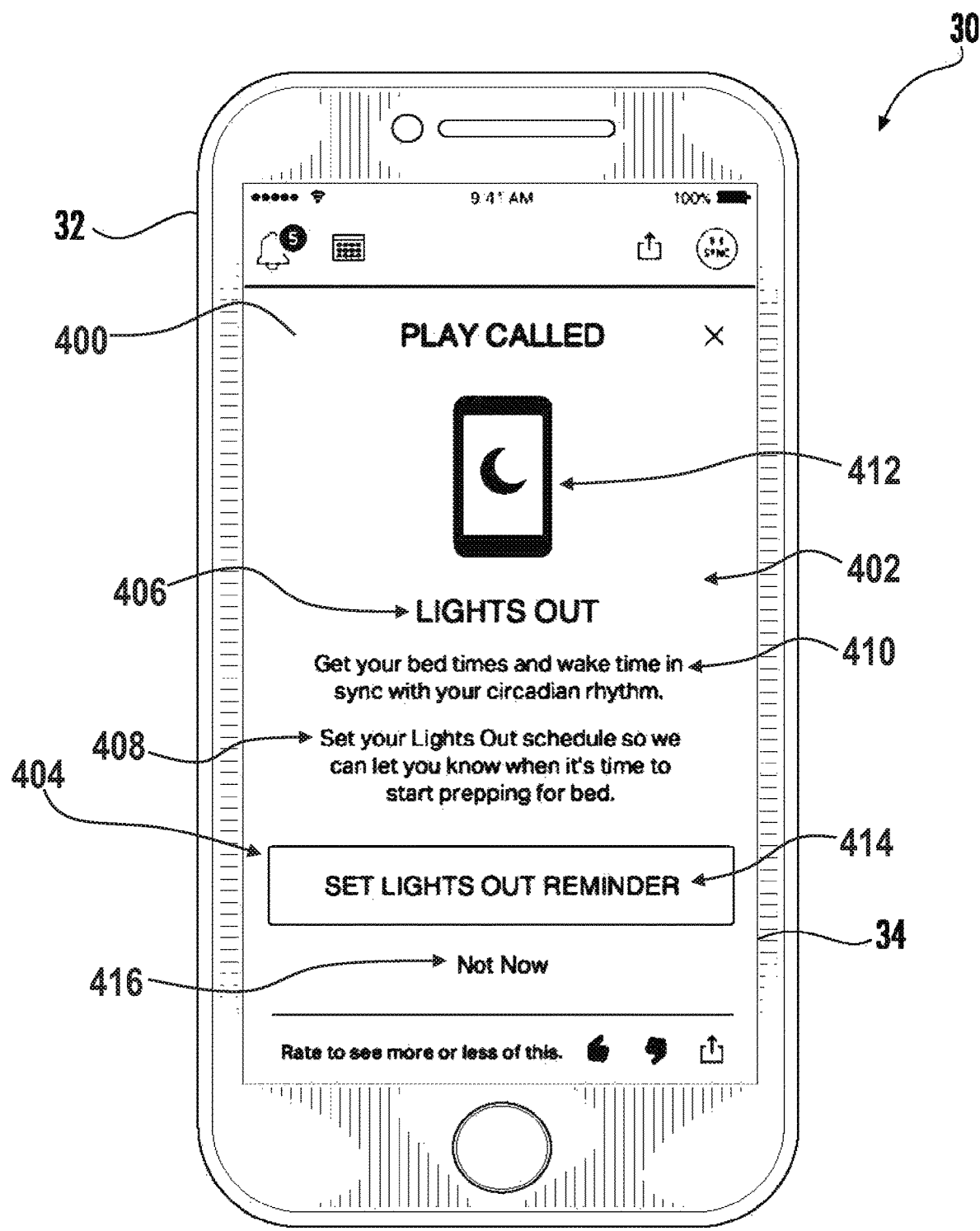
FIG. 7 shows plan view showing the electronic display device of the health tracking system of FIG. 1 displaying a health task notification screen for providing a health task notification that recommends setting a health or fitness goal.

FIG. 7 shows an exemplary embodiment of a health task notification screen 400 that is displayed on the display screen 34 of the electronic display device 30 to provide a health task notification to the user that recommends setting a health or fitness goal. Particularly, the processor 37 executes instructions of the health tracking application stored in the memory 38 to display the health task notification screen 400 on the display screen 34. In the embodiment shown and described herein, the health task notification screen 400 provides a recommendation to the user to set a sleep schedule, which defines goals for bed time, wake time, and sleep duration. However, in other embodiments, a similar health task notification screen can be used for various other plays, such as a suggestion to create a meal plan or schedule, a suggestion to create a workout plan or schedule, and/or a suggestion to set some other health or fitness goal.

Much like the health task notification screen 100, the health task notification screen 400 includes a message 402 and a prompt 404 that enables the user to provide an input in response to the message 402. The message 402 of health task notification screen 400 includes a title 406 (e.g., "Lights Out") which identifies the nature of the particular play that is provided by the health task notification screen 400 (e.g., a recommendation to set a sleep schedule). Additionally, the message 402 of the health task notification screen 400 includes a summary 408 (e.g. "Set your Lights Out schedule so we can let you know when it's time to start prepping for bed.") which conveys the content of the particular play, which generally includes a recommendation to perform a particular health task (e.g., to set a sleep schedule.). Finally, the message 402 of the health notification screen 400 optionally includes detailed guidance 410 which provides additional information and context to the user about the health and fitness benefits of performing the recommended health task (e.g., "Get your bed times and wake time in sync with your circadian rhythm."). In the embodiment shown, the message 402 of the health notification screen 400 further includes an icon 412. The icon 412 is generally indicative of the health or fitness topic about which the play pertains (e.g., a crescent moon icon is used for sleep related plays).

As mentioned above, the health task notification screen 400 also includes a prompt 404 that enables the user to provide an input in response to the message 402. In the illustrated embodiment, the prompt 404 includes at least two options that are selectable by the user to provide an input in response to the message 402. In the embodiment shown, the prompt 404 includes a set-up option 414 (e.g., "Set Lights Out Reminder") indicating that the user would like to set the respective health or fitness goal (e.g., set a sleep schedule), and a dismissal option 416 (e.g., "Not Now") indicating that the user does not want to set the respective health or fitness goal at this time. In response to the user pressing one of the options 414, 416 on the screen 34, the I/O interface 36 is configured to provide the selection of the user to the processor 37 and/or the processor 37 is configured to determine which of the options 414, 416 was selected based on input information received from the I/O interface 36.

Figure 8:
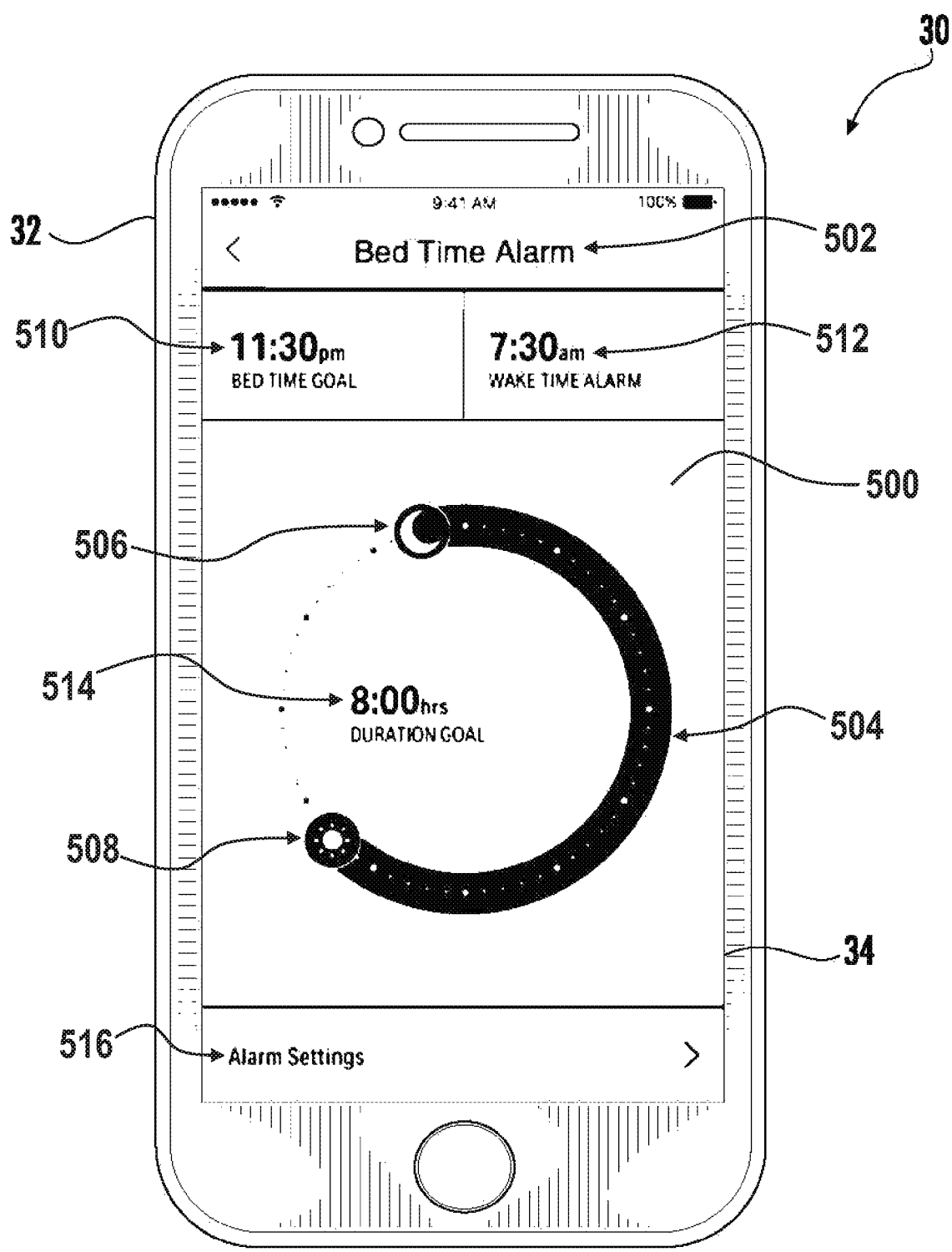
FIG. 8 shows plan view showing the electronic display device of the health tracking system of FIG. 1 displaying a bed time alarm screen for setting or adjusting bed time and wake time goals.

In response the user selecting the set-up option 414 (e.g., "Set Lights Out Reminder"), the processor 37 displays a further prompt and/or setup screen on the display screen 34 that enables the user to establish the respective health or fitness goal (e.g., set a sleep schedule, set a workout schedule, set a meal schedule, etc.). FIG. 8 shows an exemplary embodiment of a goal setup screen 500 that is displayed on the display screen 34 of the electronic display device 30 once the user has selected the set-up option 414 (e.g., "Set Lights Out Reminder"). The goal setup screen 500 enables the user to set or adjust his or her bed time, wake time, and sleep duration goals in the illustrated embodiment. However, it is appreciated that other goals may be used consistent with the herein described features, such as the previously referenced workout goals, food logging goals, activity goals, etc. Accordingly, the user may enter workout days and/or times, meal times, etc.

In the embodiment shown, the goal setup screen 500 includes a title 502 (e.g., "Bed Time Alarm") which identifies the nature of the particular health and fitness goals that are being set (e.g., goals relating a sleep schedule). In the illustrated embodiment, the goal setup screen 500 further includes a goal setting tool 504 having a bed time slider 506 and a wake time slider 508. It is appreciated that these same sliders may be used for setting workout reminders, meal logging reminders, etc. in much the same manner as discussed herein.

In the embodiment shown, the goal setting tool 504 has a generally circular shape and the sliders 506, 508 are slid around the circumference of the goal setting tool 504 to adjust a bed time goal, a wake time goal, and a sleep duration goal. Particularly, the user can touch the screen 34 to position the bed time slider 506 at a position corresponding to a desired bed time goal. Similarly, the user can also touch the screen 34 to position the wake time slider 508 at a position corresponding to a desired wake time goal. The relative positioning of the bed time slider 506 and the wake time slider 508 around the circumference of the goal setting tool 504 defines a sleep duration goal. The goal setup screen 500 includes a bed time goal indicator 510 (e.g., "11:30 pm") that identifies the bet time goal that has been set by the user. Similarly, the goal setup screen 500 includes a wake time alarm indicator 512 (e.g., "7:30 am") that identifies the wake time goal that has been set by the user. Finally, the goal setup screen 500 includes a sleep duration goal indicator 514 (e.g., "8:00 hrs") that identifies the sleep duration goal that has been set by the user. Finally, the goal setup screen 500 includes an alarm settings option 516 (e.g., "Alarm Settings"). In response the user selecting the alarm settings option 516, the processor 37 displays a further prompt and/or setup screen (not shown) on the display screen 34 that enables the user to adjust settings for health task notifications relating to the goals that have been set using the goal setup screen 500 (e.g., settings for bedtime reminders and wake up alarms, such as sounds, etc.). Similar logic applies for diming of reminders and notifications relating to other user health tasks (e.g., the user can select the time for receiving a message to log particular meals, time for receiving a message to log a workout, etc.).

Returning to FIG. 7, in response the user selecting the dismissal option 416 (e.g., "Not Now"), the processor 37 is configured to dismiss the play from the display screen 34. In one embodiment, the health tracking application is configured to display the health task notification screen 400 again at a later time to provide the user with another opportunity to set the respective health or fitness goal consistent with his/her dismissal of a scheduled notification.

Methodology

Methods for operating the health tracking system 10 are described below. In particular, a method of operating an electronic display device to provide a bedtime reminder is provided. It is appreciated that the method may equally apply to any number of other health tasks, the foregoing being merely exemplary of the general concept. In the description of the methods, statements that a method is performing some task or function refers to a controller or general purpose processor executing programmed instructions stored in non-transitory computer readable storage media operatively connected to the controller or processor to manipulate data or to operate one or more components in the health tracking system 10 to perform the task or function. Particularly, the processor 37 of the display device 30 and/or the processor 27 of the health monitoring device 20 above may be such a controller or processor. Alternatively, the controller or processor may be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

Figure 9:
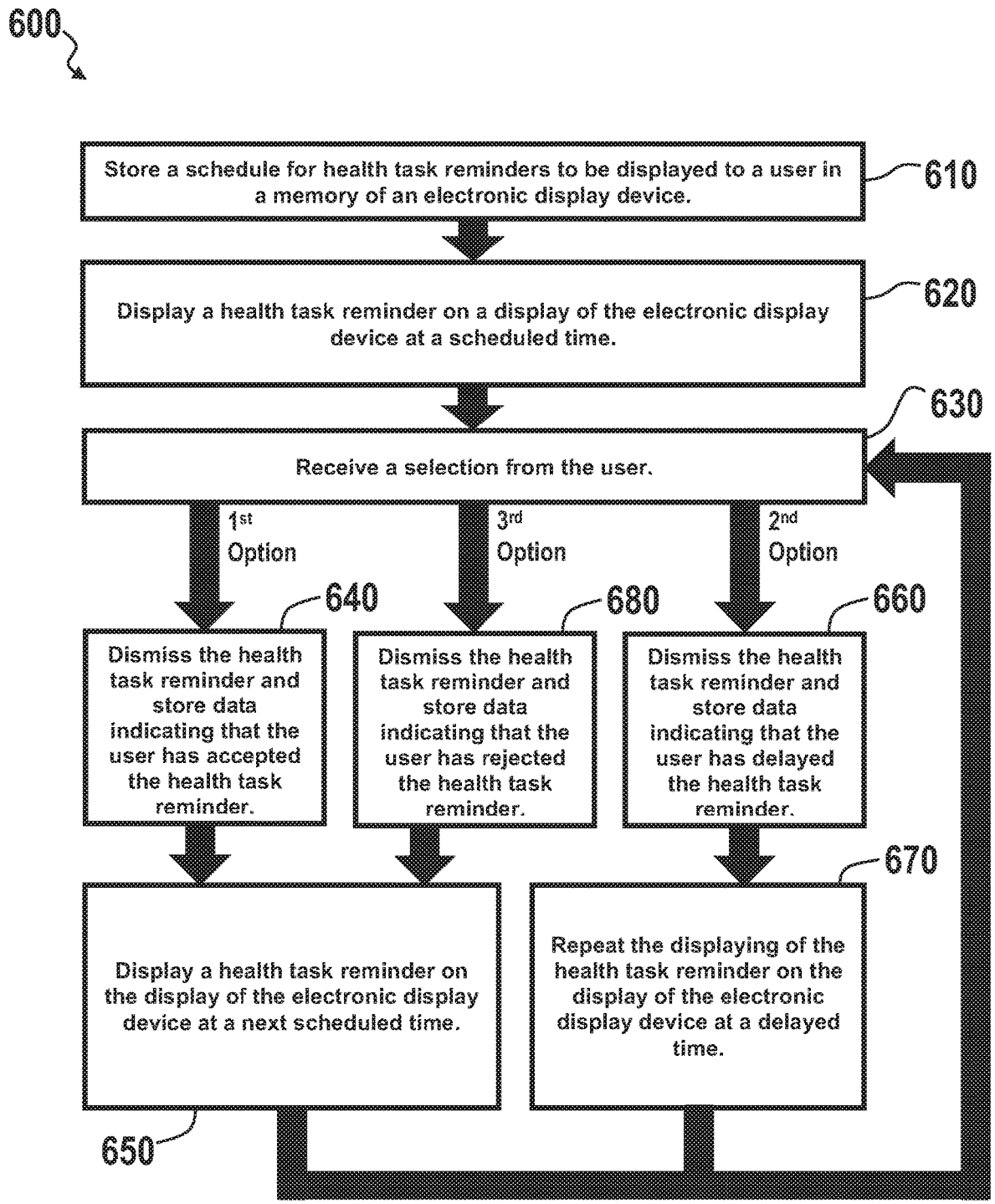
FIG. 9 shows a logical flow diagram showing a method of operating an electronic display device to provide a bedtime reminder.

FIG. 9 shows a logical flow diagram showing a method 600 of operating an electronic display device to provide a health task reminder. The method 600 begins with a step of storing a schedule for health task reminders to be displayed to a user in a memory of an electronic display device (block 610). Particularly, the processor 37 is configured to execute instructions of a health tracking application stored in the memory 38 to store a schedule for times at which health task reminder notifications should be displayed to the user in the memory 38. The schedule may be manually created by the user, may be based on a default schedule based on the user's inputted health goals, and/or may comprise a user modified default schedule (modified either manually or via learned patterns based on the user's interactions with previous notifications).

The method 600 continues with a step of displaying a health task reminder on a display of the electronic display device at a specific time based on the schedule, the health task reminder includes a prompt by which the user may interact with the notification (block 620). In one embodiment, the interaction comprises selection of one of at least three options. Particularly, the processor 37 is configured to operate the display screen 34 to display a health task reminder notification, such the health task notification screen 100, at a scheduled time based on the stored schedule. Alternatively, or in addition, the notification may comprise a summarized notification displayed on the lock screen and which is expandable via unlocking the phone.

The method 600 continues with a step of receiving, after the displaying of the health task reminder, the user interaction or selection via an input device thereof at the electronic display device (block 630). Particularly, the processor 37 is configured to determine which of the options was selected based on input information received from the I/O interface 36 and/or the I/O interface 36 is configured to provide the selection of the user to the processor 37.

In response to the user indicating an acceptance of the health task notification, the method 600 continues (block 640) by completing the display of the notification. In this instance the completion thereof comprises dismissing the health task reminder. Additionally, data indicating that the user has accepted the health task reminder is stored. Specifically, the processor 37 is configured to operate the display screen 34 to dismiss the health task reminder from the display screen 34 and/or stop displaying health task reminder on the display screen 34. Additionally, the processor 37 may be configured to generate and/or modify a data record for the user to indicate that the user has accepted the health task reminder. The method 600 continues with a step of displaying a second health task reminder on the display of the electronic display device at a next scheduled time (block 650). The second health task reminder may comprise the same or similar content to the first reminder, or alternatively, may comprise a message having different content, tone, length, etc. In one variant, at the next scheduled time, the second health task reminder may include interaction options such as those discussed above. The processor 37 is configured to operate the display screen 34 to display a health task reminder notification, such the health task notification screen 100, at the next scheduled time based on the stored schedule. At this point, the method 600 continues with regard to a receipt of a selection from the user (block 630).

In response to the user indicating a delay of the health task notification, the method 600 continues (block 660) by completing the display of the notification. In this instance the completion thereof comprises temporarily dismissing the health task reminder. Additionally, data indicating that the user has delayed the health task reminder is stored. Particularly, the processor 37 is configured to operate the display screen 34 to dismiss the health task reminder from the display screen 34 and/or stop displaying health task reminder on the display screen 34. Additionally, the processor 37 may be configured to generate and/or modify a data record for the user to indicate that the user has delayed the health task reminder. As discussed elsewhere herein, this data may be used to determine whether the date and/or time scheduled for the notification should be permanently adjusted (such as when a threshold number of responses indicating a delay or a pattern of delays at a particular date/time are received).

In the case the health task reminder was delayed, the method 600 continues with a step of repeating the displaying of the health task reminder on the display of the electronic display device according to a time delay period, the time delay period comprising a predetermined amount of time after the scheduled time or last selection of the delay option (block 670). This may be accomplished via a temporary modification to the schedule or may occur outside of any modifications to the schedule (i.e., may be performed independent of the schedule). Specifically, the processor 37 is configured to operate the display screen 34 to display again the previous health task reminder notification at a delayed time that is predetermined amount of time after the originally scheduled time and/or a predetermined amount of time after the user selected the second option to delay the health task reminder. The notification may contain a plurality of selectable options as discussed elsewhere herein. In another embodiment, the previously referenced counter may be updated and configured to once a threshold number is met, limit the user's choices. For example, the user may only be allowed to delay a message a certain number of times before he/she must either accept or dismiss it. At this point, the method 600 continues with regard to receipt of a selection from the user (block 630).

In response to the user indicating a dismissal of the health task notification, the method 600 continues (block 680) by completing the display of the notification. In this instance the completion thereof comprises dismissing the health task reminder. Additionally, data indicating that the user has dismissed the health task reminder is stored. Specifically, the processor 37 is configured to operate the display screen 34 to dismiss the health task reminder from the display screen 34 and/or stop displaying health task reminder on the display screen 34. Additionally, the processor 37 may be configured to generate and/or modify a data record for the user to indicate that the user has rejected the health task reminder. As discussed elsewhere herein, this data may be used to determine whether the date and/or time scheduled for the notification should be permanently adjusted (such as when a threshold number of responses indicating a dismissal or a pattern of dismissals at a particular date/time are received). In the case the health task reminder was rejected, the method 600 continues with a step of displaying a second health task reminder on the display of the electronic display device at a next scheduled time, the second health task reminder including a prompt with which the user can interact. The second health task reminder may comprise different or the same content, length and/or tone as the first health task reminder based at least in part on e.g., a determination of a pattern of positive or negative reactions to certain content, lengths and/or tone. In one embodiment, the interaction comprises a selection from among a plurality of options (block 650). At this point, the method 600 continues with regard to receipt a selection from the user (block 630).

The herein described applications (e.g., health tracking applications) improve the functioning of the electronic display device 30 and/or the health tracking devices 20, respectively or in combination by enabling it/them to encourage and guide the user in achieving his or her health and fitness goals without burdening or annoying the user so much that he or she might disable the features or abandon use of the health tracking system 10 entirely. Furthermore, devices that are able to intelligently schedule and reschedule health task notifications can operate more efficiently to provide health task notifications only when desired by the user, thereby saving processing time and battery life. Moreover, devices that are able to learn a user's preferences based on interactions with reminders or notifications enable the user to interact more meaningfully with the systems thereof.

The foregoing detailed description of one or more exemplary embodiments of the health tracking system has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

What is claimed is:

1. A method of operating a user device, the method comprising:
    storing a schedule for a display of a plurality of health task reminders to a user;
    displaying one of the plurality of health task reminders on a display device of the user device at a first day and/or time based on the schedule;
    displaying three options on the display device simultaneously with the health task reminder at the first day and/or time, the three options including a first option to accept the health task reminder, a second option to temporarily alter the first day and/or time of the health task reminder, and a third option to reject the health task reminder;
    receiving user input relating to the health task reminder via an input device of the user device, the user input including a selection of one of the three options on the display device;
    performing an action based on the user input;
    determining, based at least in part on the data indicative of the user input, whether to modify the schedule, the modification comprising:
        when the user input is selection of the first option or the third option, removing the health task reminder scheduled for the first day and/or time;

when the user input is selection of the second option or third option for more than a threshold number of times, permanently altering a scheduled day and/or time of the health task reminder; and when the user input is selection of the second option, temporarily altering the first day and/or time of the health task reminder; and when it is determined to modify the schedule:
storing the modified schedule; and
displaying the health task reminders on the display device of the user device according to the modified schedule.

2. The method of claim 1, wherein when the user input comprises selection of the first option to accept the health task reminder:
the act of performing an action comprises completion of the display of the health task reminder;
the act of determining comprises determining not to modify the schedule; and
the method further comprises continuing to display the health task reminder at subsequent iterations of the first day and/or time according to the schedule.

3. The method of claim 1, wherein when the user input comprises selection of the third option to reject the health task reminder:
the act of performing an action comprises completion of display of the health task reminder;
the act of determining comprises determining to modify the schedule by removing the health task reminder for the first day and/or time; and
when the third option has been selected more than the threshold number of times, the method further comprises omitting to display the health task reminder at subsequent iterations of the first day and/or time according to the modified schedule.

4. The method of claim 1, wherein when the user input comprises selection of the second option to temporarily alter the health task reminder:
the act of performing an action comprises after a predetermined delay period, re-displaying the health task reminder and adjusting a count indicative of a number of user inputs indicating a delay which have been received;
when the number of user inputs indicating a delay exceeds a predetermined threshold:
the act of determining comprises determining to modify the schedule by removing the health task reminder for the first day and/or time; and
the method further comprises omitting to display the health task reminder at subsequent iterations of the first day and/or time according to the modified schedule; and
when the number of user inputs indicating a delay does not exceed the predetermined threshold:
the act of determining comprises determining to modify the schedule by altering the day and/or time; and
the method further comprises displaying the health task reminder at subsequent iterations of the first day and/or time according to the modified schedule.

5. The method of claim 1, further comprising providing a user interface for enabling a user to establish the schedule of health task reminders consistent with a health goal.

6. The method of claim 1, wherein the health task reminders comprise at least one of:
a reminder that the user should prepare for sleep;
a reminder that the user should log a workout; and
a reminder that the user should log consumption of food.

7. The method of claim 1 wherein the health task reminder comprises a reminder that the user should prepare for sleep, and the method further comprises:
receiving data from a sensor in communication with the user device;
determining based on the data whether the user has fallen asleep within a predetermined amount of time after receiving the user input of the first option indicating an acceptance of the health task reminder;
when it is determined that the user has not fallen asleep within the predetermined amount of time, adding a message to the schedule which describes the value of achieving a sleep goal; and
when it is determined that the user has fallen asleep within the predetermined amount of time, recording the user's progress toward the sleep goal.

8. A computer readable apparatus comprising a plurality of executable instructions which are configured to, when executed by a processor:
store, at a storage apparatus of a user device, a schedule indicating a day and/or time for a plurality of health task reminders to be displayed to a user;
display, at a display apparatus of a user device, a heath task reminder at a first day and/or time based on the schedule;
display, at the display apparatus simultaneously with the health task reminder, three options including a first option to accept and remove the health task reminder, a second option to reject and temporarily alter the day and/or time of the health task reminder, and a third option to reject and remove the health task reminder;
receive user input relating to the health task reminder, the user input comprising a selection of one of the first option, the second option, or the third option;
complete the display of the health task reminder based on the user input;
process the user input to determine whether to modify the schedule, the modification comprising:
when the user input is selection of the first option or third option, removal of the health task reminder scheduled for the first day and/or time; and
when the user input is selection of the second or third option for more than a threshold number of times, alteration of a day and/or time of the health task reminder scheduled for the first day and/or time;
when the user input is selection of the second option, temporary alteration of the day and/or time of the health task reminder for the first day and/or time;
when it is determined to modify the schedule:
storing the modified schedule; and
displaying the health task reminder on a display of the electronic display device according to the modified schedule; and
when it is determined not to modify the schedule, continuing display of the plurality of health task reminders according to the schedule.

9. The computer readable apparatus of claim 8, wherein the completion of the display comprises one of:
causing the health task reminder to be temporarily removed from the display, then after a predetermined delay period, re-displaying the health task reminder; and
causing the health task reminder to be removed from the display at least until a next iteration of the first day and/or time according to the schedule or the modified schedule.

10. The computer readable apparatus of claim 8, wherein the determination is made to modify the schedule when the user input comprises one of: dismissal of the health task reminder based on selection of the third option or a delay of the health task reminder based on selection of the second option.

11. The computer readable apparatus of claim 8, wherein the determination is made not to modify the schedule when the user input comprises an acceptance of the health task reminder based on selection of the first option.

12. The computer readable apparatus of claim 8, wherein the plurality of executable instructions are further configured to, when executed by the processor: provide an interface configured to enable a user to create the schedule of health task reminders consistent with a health goal.

13. The computer readable apparatus of claim 8, wherein the plurality of executable instructions are further configured to, when executed by the processor:
 receive data from a sensor in communication with the user device; and
 determine based on the data whether the user performed the health task.

14. The computer readable apparatus of claim 13, wherein:
 when it is determined that the user has not performed the health task, adding a message to the schedule which provides information relating to the unperformed health task; and
 when it is determined that the user has performed the health task, recording the user's progress toward the health goal.

15. The computer readable apparatus of claim 13, wherein the health task reminder comprises a reminder that the user should prepare for sleep, and the data from the sensor comprises data indicative of a time at which the user fell asleep.

16. A user device comprising:
 a display apparatus configured to provide a display to a user;
 an input apparatus configured receive inputs from the user;
 a storage apparatus; and
 a processor configured to execute at least one computer application thereon, the computer application comprising a plurality of instructions stored at the storage apparatus and which are configured to, when executed, cause the user device to:
  store a schedule, the schedule indicating a day and/or time for each of a plurality of health task notifications to be displayed to the user;
  display a heath task notification at a first day and/or time based on the schedule;
  display simultaneously with the health task notification, three options including a first option to acknowledge the health task reminder, a second option to delay the day and/or time of the health task reminder, and a third option to dismiss the health task reminder;
  receive user input relating to the health task notifications, the user input comprising a selection of one of the first option, the second option, or the third option;
  process the user input to: (i) when the user input is selection of the third option for more than a threshold number of times, remove the health task notification from the first day and/or time and generate a modified schedule, (ii) when the user input is selection of the second option, alter the first day and/or time of the health task notification to generate the modified schedule, or (iii) when the user input is selection of the first option or selection of the third option for less than the threshold number of times, make no modifications to the schedule and omitting to generate the modified schedule;
  continue to display the plurality of health task notifications to the user according to the modified schedule when a modified schedule is generated and according to the schedule when generation of the modified schedule is omitted.

17. The user device of claim 16, wherein the health task notifications comprise at least one of:
 a notification that the user should prepare for sleep;
 a notification that the user should log a workout; and
 a notification that the user should log consumption of food.

18. The user device of claim 16, wherein the plurality of instructions are further configured to, when executed, cause the user device to:
 complete the display of the health task notifications based on the user input, the completion comprising: causing the health task reminder to be temporarily removed from the display, then after a predetermined delay period, re-displaying the health task reminder; and causing the health task reminder to be removed from the display at least until a next iteration of the first day and/or time according to the schedule or the modified schedule.

19. The user device of claim 16, wherein:
 the plurality of instructions are further configured to cause the user device to:
  receive data relating to a performance of the health task;
  based at least in part on the data, determine whether the user has completed the health task;
  based on the determination, display a secondary message to the user;
 wherein when it is determined that the user has completed the health task, the secondary message comprises a message congratulating the user; and
 wherein when it is determined that the user has not completed the health task, encouraging the user to complete the health task in a next iteration.

* * * * *